US011912962B2

(12) United States Patent
Xu et al.

(10) Patent No.: US 11,912,962 B2
(45) Date of Patent: Feb. 27, 2024

(54) FLEXIBLE, POROUS, DISSOLVABLE SOLID SHEET ARTICLES CONTAINING CATIONIC SURFACTANT

(71) Applicant: The Procter & Gamble Company, Cincinnati, OH (US)

(72) Inventors: Dan Xu, Beijing (CN); Hongsing Tan, Beijing (CN); Juan Yang, Beijing (CN); Na Hou, Beijing (CN); Carl David Mac Namara, Beijing (CN); Yongli Pan, Tianjin (CN)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 17/172,346

(22) Filed: Feb. 10, 2021

(65) Prior Publication Data
US 2021/0261892 A1  Aug. 26, 2021

(30) Foreign Application Priority Data

Feb. 20, 2020  (WO) ................ PCT/CN2020/076049

(51) Int. Cl.
C11D 17/06 (2006.01)
C11D 1/29 (2006.01)
C11D 1/38 (2006.01)
C11D 1/62 (2006.01)
C11D 1/835 (2006.01)
C11D 3/20 (2006.01)
C11D 3/22 (2006.01)
C11D 3/37 (2006.01)
C11D 17/04 (2006.01)

(52) U.S. Cl.
CPC ................ C11D 17/06 (2013.01); C11D 1/29 (2013.01); C11D 1/835 (2013.01); C11D 3/2065 (2013.01); C11D 3/2082 (2013.01); C11D 3/3753 (2013.01)

(58) Field of Classification Search
None
See application file for complete search history.

(56) References Cited

U.S. PATENT DOCUMENTS

| 4,170,565 | A | 10/1979 | Flesher et al. |
| 4,557,852 | A | 12/1985 | Schulz et al. |
| 4,610,799 | A | 9/1986 | Wilsberg et al. |
| 4,654,395 | A | 3/1987 | Schulz et al. |
| 4,743,394 | A | 5/1988 | Kaufmann et al. |
| 4,747,976 | A | 5/1988 | Yang et al. |
| 4,806,261 | A | 2/1989 | Ciallella et al. |
| 4,938,888 | A | 7/1990 | Kiefer et al. |
| 5,202,045 | A | 4/1993 | Karpusiewicz et al. |
| 6,465,407 | B2 | 10/2002 | Hayashi |

(Continued)

FOREIGN PATENT DOCUMENTS

| CA | 1242949 A | 10/1988 |
| CN | 1202517 A | 12/1998 |

(Continued)

OTHER PUBLICATIONS

International Search Report and Written Opinion; Application Ser. No. PCT/CN2020/076049; dated Sep. 30, 2020; 14 pages.

(Continued)

Primary Examiner — Lorna M Douyon

(57) ABSTRACT

This provides a flexible, porous, dissolvable solid sheet article containing a cationic surfactant.

14 Claims, 5 Drawing Sheets

(56) References Cited

U.S. PATENT DOCUMENTS

| | | | |
|---|---|---|---|
| 6,699,826 B1 | 3/2004 | Saijo | |
| 6,818,606 B1 | 11/2004 | Hanada | |
| 7,094,744 B1 | 8/2006 | Kobayashi | |
| 8,367,596 B2 | 2/2013 | Fossum et al. | |
| 8,425,622 B2* | 4/2013 | Felts | A61K 8/416 8/405 |
| 9,233,055 B2 | 1/2016 | Glenn, Jr. et al. | |
| 9,969,154 B2 | 5/2018 | Content et al. | |
| 2002/0091169 A1 | 7/2002 | Klotzer | |
| 2004/0220063 A1 | 11/2004 | Chappell et al. | |
| 2007/0027051 A1 | 2/2007 | Staudigel et al. | |
| 2009/0104420 A1 | 4/2009 | Nadella et al. | |
| 2009/0232873 A1 | 9/2009 | Glenn, Jr. et al. | |
| 2009/0263342 A1* | 10/2009 | Glenn, Jr. | A61K 8/345 424/70.11 |
| 2010/0286011 A1 | 11/2010 | Glenn, Jr. et al. | |
| 2010/0298188 A1* | 11/2010 | Glenn, Jr. | A61K 8/8129 264/293 |
| 2011/0023240 A1* | 2/2011 | Fossum | C11D 3/37 510/331 |
| 2011/0028374 A1* | 2/2011 | Fossum | C11D 17/00 510/296 |
| 2011/0136719 A1 | 6/2011 | Jalbert | |
| 2011/0319311 A1 | 12/2011 | Labeque et al. | |
| 2012/0270029 A1 | 10/2012 | Glenn, Jr. et al. | |
| 2015/0159330 A1 | 6/2015 | Weisman et al. | |
| 2015/0218497 A1 | 8/2015 | Jalbert et al. | |
| 2017/0234618 A1 | 8/2017 | Guo | |
| 2019/0350819 A1 | 11/2019 | Hamersky et al. | |
| 2020/0308517 A1* | 10/2020 | Tan | B32B 3/02 |
| 2021/0163698 A1* | 6/2021 | Mac Namara | C08J 9/0033 |
| 2021/0363472 A1* | 11/2021 | Tan | A61K 8/0216 |

FOREIGN PATENT DOCUMENTS

| | | |
|---|---|---|
| CN | 2352536 Y | 12/1999 |
| CN | 1250085 A | 4/2000 |
| CN | 1421519 A | 6/2003 |
| CN | 1583991 A | 2/2005 |
| CN | 102492573 A | 6/2012 |
| CN | 202744521 | 2/2013 |
| CN | 202754982 U | 2/2013 |
| CN | 102732392 B | 9/2013 |
| CN | 103740490 A | 4/2014 |
| CN | 105199887 A | 12/2015 |
| CN | 105238584 A | 1/2016 |
| CN | 105462733 A | 4/2016 |
| CN | 105586165 A | 5/2016 |
| CN | 105647716 A | 6/2016 |
| CN | 205398584 U | 7/2016 |
| CN | 105861168 A | 8/2016 |
| CN | 105886142 A | 8/2016 |
| CN | 205420320 U | 8/2016 |
| CN | 106635572 A | 5/2017 |
| JP | H04202600 A | 7/1992 |
| JP | 4509284 B2 | 5/2010 |
| KR | 20080111815 A | 12/2008 |
| KR | 20090036882 A | 4/2009 |
| KR | 20090036883 A | 4/2009 |
| KR | 20100090122 A | 8/2010 |
| KR | 20100096985 A | 9/2010 |
| KR | 101146292 B1 | 5/2012 |
| KR | 20120127174 A | 11/2012 |
| KR | 20120130693 A | 12/2012 |
| WO | 2005039517 A1 | 5/2005 |
| WO | 2012157851 A1 | 11/2012 |
| WO | 2012166478 A2 | 12/2012 |
| WO | 2014078976 A1 | 5/2014 |

OTHER PUBLICATIONS

PCT Supplementary Search Report and Written Opinion for PCT/CN2020/076049 dated Jun. 17, 2022, 12 pages.

\* cited by examiner

FLEXIBLE, POROUS, DISSOLVABLE SOLID SHEET ARTICLES CONTAINING CATIONIC SURFACTANT

FIELD OF THE INVENTION

The present invention relates to a flexible, porous, dissolvable solid sheet article containing a cationic surfactant.

BACKGROUND OF THE INVENTION

Flexible dissolvable solid sheets comprising surfactant(s) and/or other active ingredients in a water-soluble polymeric carrier or matrix are well known. The water-soluble polymer may function in the solid sheets as a film-former, a structurant as well as a carrier for other ingredients. Such sheets may be used as fabric care products, home care products, hair care products, beauty care products, personal care products and the like. Particularly, such flexible dissolvable sheets may comprise a cationic surfactant as a fabric care active (for example fabric conditioner), a home care active (for example a dish cleaner), a hair care active (for example hair conditioner), a beauty care active and/or a personal care active and may be particularly useful for delivering such active upon dissolution in water. In comparison with traditional liquid forms of fabric care, home care, hair care, beauty care and/or personal care products in the same product category, such sheets have better structural integrity, are more concentrated and easier to store, ship/transport, carry, and handle. In comparison with the solid tablet form in the same product category, such sheets are more flexible and less brittle, with better sensory appeal to the consumers.

To improve dissolution, WO2010077627 discloses a batch process for forming porous sheets with open-celled foam (OCF) structures characterized by a Percent Open Cell Content of from about 80% to 100%. Specifically, a pre-mixture of raw materials comprising a water-soluble polymeric carrier is first formed, which is vigorously aerated to introduce air bubbles in the pre-mixture and then heat-dried in batches (e.g., in a convection oven or a microwave oven) to form the porous sheets with the desired OCF structures. However, it was discovered by the inventor of the present invention that, in the process for forming porous solid sheets containing a cationic surfactant, the aerated pre-mixture might be less stable than desired. In other words, the formed bubbles in the aerated pre-mixture might collapse in a short time after the aeration. In this case, the formed porous sheets may have a Percent Open Cell Content lower than expected, or the aerated pre-mixture needs to be heat-dried as soon as possible or even immediately after the aeration to ensure formation of the desired OCF structures. This may bring about undesirable difficulties in designing a manufacturing process of such porous sheets, especially in large-scale production, because it might not be realistic to dry the aerated pre-mixture immediately after the aeration without any intervals in industrial production.

There is therefore a need for improving stability of the aerated pre-mixture in the process for forming porous sheets containing a cationic surfactant so as to obtain porous sheets having a further improved porosity and/or facilitate industrial production.

SUMMARY OF THE INVENTION

The present invention provides a flexible, porous, dissolvable solid sheet article comprising a water-soluble polymer, a plasticizer and a cationic surfactant, wherein the weight ratio of the plasticizer over the cationic surfactant is from about 0.9 to about 2. Further, the present invention provides a process of preparing the solid sheet article, wherein the process comprises a) preparing a wet pre-mixture comprising a water-soluble polymer, a plasticizer and a cationic surfactant in which the weight ratio of the plasticizer over the cationic surfactant is from about 0.9 to about 2; b) aerating the wet pre-mixture to form an aerated wet pre-mixture; c) forming the aerated wet pre-mixture into a sheet; and d) drying the formed sheet. Particularly, the weight ratio of the plasticizer over the cationic surfactant may be from about 1 to about 1.8, preferably from about 1.1 to about 1.7, and more preferably from about 1.2 to about 1.6.

Surprisingly, inventors of the present invention have unexpectedly discovered that, when the ratio of the plasticizer and the cationic surfactant in the pre-mixture is within a preferred range, e.g. from about 0.9 to about 2, the stability of the aerated pre-mixture may be significantly increased. The improved stability may further bring about a significantly improved pore structures and thereby a significantly improved dissolution profile that is desirable for consumers. Also, the improved stability may bring about significantly improved flexibility for the manufacturing process of the solid sheet article.

In one aspect, the present invention relates to a flexible, porous, dissolvable solid sheet article comprising a water-soluble polymer, a plasticizer and a cationic surfactant, wherein the solid sheet article is characterized by: (i) a Percent Open Cell Content of from about 80% to about 100%; and (ii) an Overall Average Pore Size of from about 100 μm to about 2000 μm; and wherein the weight ratio of the plasticizer over the cationic surfactant may be from about 0.9 to about 2.

The solid sheet article may preferably comprise from about 1% to about 65%, preferably from about 10% to about 60%, more preferably from about 15% to about 55%, yet more preferably from 20% to 50%, most preferably from 22% to 40%, of the plasticizer by total weight of the solid sheet article. In a preferred but not necessary embodiment of the present invention, the plasticizer may be glycerin.

The solid sheet article may preferably comprise from about 1% to about 50%, preferably from about 5% to about 45%, more preferably from about 10% to about 40%, most preferably from about 15% to about 35%, of the cationic surfactant by total weight of the solid sheet article. In a preferred but not necessary embodiment of the present invention, the cationic surfactant may be selected from the group consisting of N,N-di(acyl-oxyethyl)-N,N-dimethylammonium chloride, N,N-di(acyl-oxyisopropyl)-N,N-dimethylammonium methylsulfate, N,N-di(acyl-oxyethyl)-N,N-methylhydroxyethylammonium methylsulfate, C12-C22 alkyl trimethyl ammonium bromide, C12-C22 alkyl trimethyl ammonium chloride for example coconut trimethyl ammonium chloride and lauryl trimethyl ammonium chloride, and any combinations thereof. Preferably, the acyl group is derived from animal fats, unsaturated, and polyunsaturated, fatty acids.

The solid sheet article may preferably comprise from about 1% to about 60%, preferably from about 5% to about 50%, more preferably from about 10% to about 45%, most preferably from about 15% to about 40%, of the water-soluble polymer by total weight of the solid sheet article. In a preferred but not necessary embodiment of the present invention, the water-soluble polymer may be selected from the group consisting of polyvinyl alcohols, starch, and any combinations thereof.

Furthermore, in a preferred but not necessary embodiment of the present invention, the solid sheet article may comprise from 0.01% to about 20%, preferably from 0.1% to about 12%, more preferably from 0.5% to about 8%, most preferably from 1% to 5%, of a non-ionic surfactant by total weight of the solid sheet article.

The flexible, porous, dissolvable solid sheet article of the present invention may further be characterized by:
- a Percent Open Cell Content of from 85% to 100%, preferably from 90% to 100%; and/or
- an Overall Average Pore Size of from 150 μm to 1000 μm, preferably from 200 μm to 600 μm; and/or
- an Average Cell Wall Thickness of from 5 μm to 200 μm, preferably from 10 μm to 100 μm, more preferably from 10 μm to 80 μm; and/or
- a final moisture content of from 0.5% to 25%, preferably from 1% to 20%, more preferably from 3% to 15%, by weight of the solid sheet article; and/or
- a thickness of each sheet being from 0.5 mm to 4 mm, preferably from 0.7 mm to 3 mm, more preferably from 0.8 mm to 2 mm, most preferably from 1 mm to 1.5 mm; and/or
- a basis weight of from 50 grams/m$^2$ to 250 grams/m$^2$, preferably from 80 grams/m$^2$ to 230 grams/m$^2$, more preferably from 100 grams/m$^2$ to 220 grams/m$^2$; and/or
- a density of from 0.05 grams/cm$^3$ to 0.5 grams/cm$^3$, preferably from 0.06 grams/cm$^3$ to 0.4 grams/cm$^3$, more preferably from 0.07 grams/cm$^3$ to 0.3 grams/cm$^3$, most preferably from 0.08 grams/cm$^3$ to 0.25 grams/cm$^3$; and/or
- a Specific Surface Area of from 0.03 m$^2$/g to 0.25 m$^2$/g, preferably from 0.04 m$^2$/g to 0.22 m$^2$/g, more preferably from 0.05 m$^2$/g to 0.2 m$^2$/g, most preferably from 0.1 m$^2$/g to 0.18 m$^2$/g.

Further, the solid sheet article of the present invention may comprise two or more flexible, porous, dissolvable sheets, wherein a coating composition is present on at least one surface of at least one of the two or more sheets, provided that the coating composition is not on any of the outer surfaces of the solid sheet article.

In another aspect, the present invention relates to a process for making a sheet article, comprising the steps of: a) preparing a wet pre-mixture comprising a water-soluble polymer, a plasticizer and a cationic surfactant and having a viscosity of from about 1,000 cps to about 25,000 cps measured at 40° C. and 1 s$^{-1}$, wherein the weight ratio of the plasticizer over the cationic surfactant is from about 0.9 to about 2; b) aerating the wet pre-mixture to form an aerated wet pre-mixture having a density of from about 0.05 to about 0.7 g/ml, preferably from about 0.15 g/ml to about 0.6 g/ml, more preferably from about 0.2 g/ml to about 0.5 g/ml, most preferably from about 0.25 g/ml to about 0.45 g/ml; c) forming the aerated wet pre-mixture into a sheet having opposing first and second sides; and d) drying the formed sheet to make the sheet article. Preferably, the step d) may be conducted for a duration from about 5 min to about 300 min, preferably from about 10 min to about 120 min. Preferably, the drying in the step d) may be conducted at a temperature from about 70° C. to about 200° C., preferably from about 90° C. to about 140° C., along a heating direction that forms a temperature gradient decreasing from the first side to the second side of the formed sheet, wherein the heating direction is substantially opposite to the gravitational direction for more than half of the drying time, preferably for more than 75% of the drying time.

These and other aspects of the present invention will become more apparent upon reading the following detailed description of the invention.

DETAILED DESCRIPTION OF THE INVENTION

I. Definitions

Figure 1:
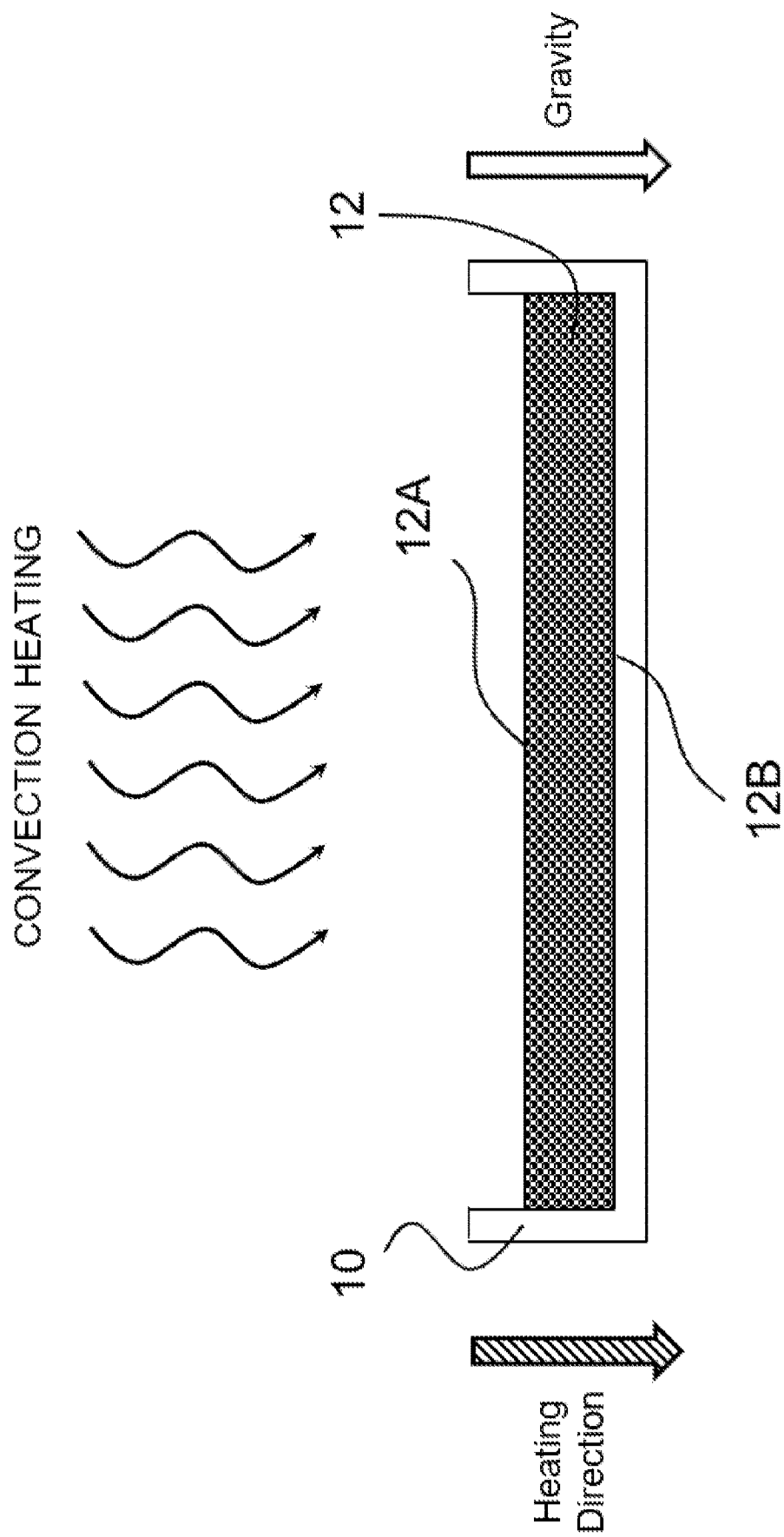
FIG. 1 shows a convection-based heating/drying arrangement for making a flexible, porous, dissolvable solid sheet article in a batch process.

The term "flexible" as used herein refers to the ability of an article to withstand stress without breakage or significant fracture when it is bent at 90° along a center line perpendicular to its longitudinal direction. Preferably, such article can undergo significant elastic deformation and is characterized by a Young's Modulus of no more than 5 GPa, preferably no more than 1 GPa, more preferably no more than 0.5 GPa, most preferably no more than 0.2 GPa.

The term "dissolvable" as used herein refers to the ability of an article to completely or substantially dissolve in a sufficient amount of deionized water at 20° C. and under the atmospheric pressure within eight (8) hours without any stirring, leaving less than 5 wt % undissolved residues.

The term "solid" as used herein refers to the ability of an article to substantially retain its shape (i.e., without any visible change in its shape) at 20° C. and under the atmospheric pressure, when it is not confined and when no external force is applied thereto.

The term "sheet" as used herein refers to a non-fibrous structure having a three-dimensional shape, i.e., with a thickness, a length, and a width, while the length-to-thickness aspect ratio and the width-to-thickness aspect ratio are both at least about 5:1, and the length-to-width ratio is at least about 1:1. Preferably, the length-to-thickness aspect ratio and the width-to-thickness aspect ratio are both at least about 10:1, more preferably at least about 15:1, most preferably at least about 20:1; and the length-to-width aspect ratio is preferably at least about 1.2:1, more preferably at least about 1.5:1, most preferably at least about 1.618:1.

As used herein, the term "bottom surface" refers to a surface of the flexible, porous, dissolvable solid sheet article of the present invention that is immediately contacting a supporting surface upon which the sheet of aerated wet pre-mixture is placed during the drying step, while the term "top surface" refers to a surface of the sheet article that is opposite to the bottom surface. Further, such solid sheet article can be divided into three (3) regions along its thickness, including a top region that is adjacent to its top surface, a bottom region that is adjacent to its bottom surface, and a middle region that is located between the top and bottom regions. The top, middle, and bottom regions are of equal thickness, i.e., each having a thickness that is about ⅓ of the total thickness of the sheet article.

The term "open celled foam" or "open cell pore structure" as used herein refers to a solid, interconnected, polymer-containing matrix that defines a network of spaces or cells that contain a gas, typically a gas (such as air), without collapse of the foam structure during the drying process, thereby maintaining the physical strength and cohesiveness of the solid. The interconnectivity of the structure may be described by a Percent Open Cell Content, which is measured by Test 3 disclosed hereinafter.

The term "water-soluble" as used herein refers to the ability of a sample material to completely dissolve in or disperse into water leaving no visible solids or forming no visibly separate phase, when at least about 25 grams, preferably at least about 50 grams, more preferably at least about 100 grams, most preferably at least about 200 grams, of such material is placed in one liter (1 L) of deionized water at 20° C. and under the atmospheric pressure with sufficient stirring.

The term "aerate", "aerating" or "aeration" as used herein refers to a process of introducing a gas into a liquid or pasty composition by mechanical and/or chemical means.

The term "heating direction" as used herein refers to the direction along which a heat source applies thermal energy to an article, which results in a temperature gradient in such article that decreases from one side of such article to the other side. For example, if a heat source located at one side of the article applies thermal energy to the article to generate a temperature gradient that decreases from the one side to an opposing side, the heating direction is then deemed as extending from the one side to the opposing side. If both sides of such article, or different sections of such article, are heated simultaneously with no observable temperature gradient across such article, then the heating is carried out in a non-directional manner, and there is no heating direction.

The term "substantially opposite to" or "substantially offset from" as used herein refers to two directions or two lines having an offset angle of 90° or more therebetween.

The term "substantially aligned" or "substantial alignment" as used herein refers to two directions or two lines having an offset angle of less than 90° therebetween.

The term "primary heat source" as used herein refers to a heat source that provides more than 50%, preferably more than 60%, more preferably more than 70%, most preferably more than 80%, of the total thermal energy absorbed by an object (e.g., the sheet of aerated wet pre-mixture according to the present invention).

The term "controlled surface temperature" as used herein refers to a surface temperature that is relatively consistent, i.e., with less than +1-20% fluctuations, preferably less than +/−10% fluctuations, more preferably less than +/−5% fluctuations.

The term "essentially free of" or "essentially free from" means that the indicated material is at the very minimal not deliberately added to the composition or product, or preferably not present at an analytically detectable level in such composition or product. It may include compositions or products in which the indicated material is present only as an impurity of one or more of the materials deliberately added to such compositions or products.

II. Formulations of Inventive Solid Sheet Articles

The solid sheet article of the present invention comprises a water-soluble polymer, a plasticizer and a cationic surfactant. Further, the solid sheet article of the present invention may further comprise one or more additional ingredients.

In some embodiments, the solid sheet article of the present invention may comprise two or more flexible, porous, dissolvable sheets stacked together. In this case, a coating composition may be present on at least one surface of at least one of the two or more sheets, provided that the coating composition is not on any of the outer surfaces of the solid sheet article. In other words, the coating composition may be added between sheets of the solid sheet article.

1. Water-Soluble Polymer

As mentioned hereinabove, the flexible, porous, dissolvable solid sheet article of the present invention may be formed by a wet pre-mixture that comprises a water-soluble polymer, a plasticizer and a cationic surfactant. Such a water-soluble polymer may function in the resulting solid sheet article as a film-former, a structurant as well as a carrier for other active ingredients (e.g., surfactants, emulsifiers, builders, chelants, perfumes, colorants, and the like).

Preferably, the wet pre-mixture may comprise from about 1% to about 30% of water-soluble polymer by weight of the pre-mixture, in one embodiment from about 5% to about 20% by weight of the pre-mixture of water-soluble polymer, in one embodiment from about 7% to about 15% of water-soluble polymer by weight of the pre-mixture.

After drying, it is preferred that the water-soluble polymer is present in the flexible, porous, dissolvable solid sheet article of the present invention in an amount ranging from about 1% to about 60%, preferably from about 5% to about 50%, more preferably from about 10% to about 45%, yet more preferably from about 15% to about 40%, most preferably from about 20% to about 30%, by total weight of the solid sheet article. In a particularly preferred embodiment of the present invention, the total amount of water-soluble polymer(s) present in the flexible, porous, dissolvable solid sheet article of the present invention is no more than about 25% by total weight of such article.

Water-soluble polymers suitable for the practice of the present invention may be selected those with weight average molecular weights ranging from about 5,000 to about 400,000 Daltons, more preferably from about 10,000 to about 300,000 Daltons, still more preferably from about 15,000 to about 200,000 Daltons, most preferably from about 20,000 to about 150,000 Daltons. The weight average molecular weight is computed by summing the average molecular weights of each polymer raw material multiplied by their respective relative weight percentages by weight of the total weight of polymers present within the porous solid. The weight average molecular weight of the water-soluble polymer used herein may impact the viscosity of the wet pre-mixture, which may in turn influence the bubble number and size during the aeration step as well as the pore expansion/opening results during the drying step. Further, the weight average molecular weight of the water-soluble polymer may affect the overall film-forming properties of the wet pre-mixture and its compatibility/incompatibility with certain surfactants.

The water-soluble polymers of the present invention may include, but are not limited to, synthetic polymers including polyvinyl alcohols, polyvinylpyrrolidones, polyalkylene oxides, polyacrylates, caprolactams, polymethacrylates, polymethylmethacrylates, polyacrylamides, polymethylacrylamides, polydimethylacrylamides, polyethylene glycol monomethacrylates, copolymers of acrylic acid and methyl acrylate, polyurethanes, polycarboxylic acids, polyvinyl acetates, polyesters, polyamides, polyamines, polyethyleneimines, maleic/(acrylate or methacrylate) copolymers, copolymers of methylvinyl ether and of maleic anhydride, copolymers of vinyl acetate and crotonic acid, copolymers of vinylpyrrolidone and of vinyl acetate, copolymers of vinylpyrrolidone and of caprolactam, vinyl pyrollidone/vinyl acetate copolymers, copolymers of anionic, cationic and amphoteric monomers, and combinations thereof.

The water-soluble polymers of the present invention may also be selected from naturally sourced polymers including those of plant origin examples of which include karaya gum, tragacanth gum, gum Arabic, acemannan, konjac mannan, acacia gum, gum ghatti, whey protein isolate, and soy protein isolate; seed extracts including guar gum, locust bean gum, quince seed, and psyllium seed; seaweed extracts such as Carrageenan, alginates, and agar; fruit extracts (pectins); those of microbial origin including xanthan gum, gellan gum, pullulan, hyaluronic acid, chondroitin sulfate, and dextran; and those of animal origin including casein, gelatin, keratin, keratin hydrolysates, sulfonic keratins, albumin, collagen, glutelin, glucagons, gluten, zein, and shellac.

Modified natural polymers can also be used as water-soluble polymers in the present invention. Suitable modified natural polymers include, but are not limited to, cellulose derivatives such as hydroxypropylmethylcellulose, hydroxymethylcellulose, hydroxyethylcellulose, methylcellulose, hydroxypropylcellulose, ethylcellulose, carboxymethylcellulose, cellulose acetate phthalate, nitrocellulose and other cellulose ethers/esters; and guar derivatives such as hydroxypropyl guar.

The water-soluble polymer of the present invention may include starch. As used herein, the term "starch" includes both naturally occurring or modified starches. Typical natural sources for starches can include cereals, tubers, roots, legumes and fruits. More specific natural sources can include corn, pea, potato, banana, barley, wheat, rice, sago, amaranth, tapioca, arrowroot, canna, sorghum, and waxy or high amylase varieties thereof. The natural starches can be modified by any modification method known in the art to form modified starches, including physically modified starches, such as sheared starches or thermally-inhibited starches; chemically modified starches, such as those which have been cross-linked, acetylated, and organically esterified, hydroxyethylated, and hydroxypropylated, phosphorylated, and inorganically esterified, cationic, anionic, nonionic, amphoteric and zwitterionic, and succinate and substituted succinate derivatives thereof; conversion products derived from any of the starches, including fluidity or thin-boiling starches prepared by oxidation, enzyme conversion, acid hydrolysis, heat or acid dextrinization, thermal and or sheared products may also be useful herein; and pregelatinized starches which are known in the art.

Preferred water-soluble polymers of the present invention include polyvinyl alcohols, polyvinylpyrrolidones, polyalkylene oxides, starch and starch derivatives, pullulan, gelatin, hydroxypropylmethylcelluloses, methycelluloses, and carboxymethycelluloses. More preferred water-soluble polymers of the present invention are selected from the group consisting of polyvinyl alcohols, starch and any combination thereof.

Polyvinyl alcohols may be characterized by a degree of hydrolysis ranging from about 40% to about 100%, preferably from about 50% to about 95%, more preferably from about 65% to about 92%, most preferably from about 70% to about 90%. Commercially available polyvinyl alcohols include those from Celanese Corporation (Texas, USA) under the CELVOL trade name including but not limited to, CELVOL 523, CELVOL 530, CELVOL 540, CELVOL 518, CELVOL 513, CELVOL 508, CELVOL 504; those from Kuraray Europe GmbH (Frankfurt, Germany) under the Mowiol® and POVAL™ trade names; and PVA 1788 (also referred to as PVA BP17) commercially available from various suppliers including Lubon Vinylon Co. (Nanjing, China); and combinations thereof.

In a particularly preferred embodiment of the present invention, the flexible, porous, dissolvable solid sheet article comprises from about 1% to about 60%, preferably from about 5% to about 50%, more preferably from about 10% to about 40%, yet more preferably from about 15% to about 40%, most preferably from about 20% to about 35%, by total weight of such article, of a polyvinyl alcohol having a weight average molecular weight ranging from about 80,000 to about 150,000 Daltons and a degree of hydrolysis ranging from about 80% to about 90%.

In another particularly preferred embodiment of the present invention, the flexible, porous, dissolvable solid sheet article comprises from about 1% to about 60%, preferably from about 5% to about 50%, more preferably from about 10% to about 40%, yet more preferably from about 15% to about 35%, most preferably from about 20% to about 30%, by total weight of such article, of a polyvinyl alcohol having a weight average molecular weight ranging from about 80,000 to about 150,000 Daltons and a degree of hydrolysis ranging from about 80% to about 90%, as well as from about 0.001% to about 5%, preferably from about 0.01% to about 4.5%, more preferably from about 0.1% to about 4%, yet more preferably from about 1% to about 4%, most preferably from about 2% to about 4%, by total weight of such article, of starch. The presence of starch may help to reduce the overall level of water-soluble polymers required and/or provide other benefits in terms of physical/chemical characteristics as described herein. However, while not being bound by any theory, it is believed that too much starch may compromise the solubility, structural integrity and/or the elasticity of the sheet article. Therefore, in preferred embodiments of the present invention, it is desired that the solid sheet article comprises no more than about 5%, preferably from about 0% to about 4.5%, more preferably from about 0% to about 4%, of starch by weight of the solid sheet article.

In another particularly preferred embodiment of the present invention, the flexible, porous, dissolvable solid sheet article comprises from about 1% to about 60%, preferably from about 2% to about 30%, more preferably from about 3% to about 20%, yet more preferably from about 4% to about 15%, most preferably from about 4% to about 10%, by total weight of such article, of a first polyvinyl alcohol having a weight average molecular weight ranging from about 20,000 to about 30,000 Daltons and a degree of hydrolysis ranging from about 80% to about 90%, as well as from about 2% to about 60%, preferably from about 4% to about 40%, more preferably from about 6% to about 30%, yet more preferably from about 8% to about 25%, most preferably from about 12% to about 22%, by total weight of such article, of a second polyvinyl alcohol having a weight average molecular weight ranging from about 50,000 to about 150,000 Daltons and a degree of hydrolysis ranging from about 80% to about 90%.

2. Plasticizers

The flexible, porous, dissolvable solid sheet article of the present invention comprises a plasticizer, preferably in the amount ranging from about 1% to about 65%, preferably from about 10% to about 60%, more preferably from about 15% to about 55%, yet more preferably from about 20% to about 50%, most preferably from about 22% to about 40%, by total weight of the solid sheet article. Correspondingly, the wet pre-mixture used for forming such solid sheet article may comprise from about 0.1% to about 50%, preferably from about 1% to about 40%, more preferably from about 5% to about 30%, yet more preferably from about 8% to about 25%, most preferably from about 10% to about 20%, of a plasticizer, by weight of the wet pre-mixture.

Suitable plasticizers for use in the present invention include, for example, polyols, copolyols, polycarboxylic acids, polyesters, dimethicone copolyols, and the like.

Examples of useful polyols include, but are not limited to: glycerin, diglycerin, ethylene glycol, polyethylene glycol (especially 200-600), propylene glycol, butylene glycol, pentylene glycol, glycerol derivatives (such as propoxylated glycerol), glycidol, cyclohexane dimethanol, hexanediol, 2,2,4-trimethylpentane-1,3-diol, pentaerythritol, urea, sugar alcohols (such as sorbitol, mannitol, lactitol, xylitol, maltitol, and other mono- and polyhydric alcohols), mono-, di- and oligo-saccharides (such as fructose, glucose, sucrose, maltose, lactose, high fructose corn syrup solids, and dextrins), ascorbic acid, sorbates, ethylene bisformamide, amino acids, and the like.

Examples of polycarboxylic acids include, but are not limited to citric acid, maleic acid, succinic acid, polyacrylic acid, and polymaleic acid.

Examples of suitable polyesters include, but are not limited to, glycerol triacetate, acetylated-monoglyceride, diethyl phthalate, triethyl citrate, tributyl citrate, acetyl triethyl citrate, acetyl tributyl citrate.

Examples of suitable dimethicone copolyols include, but are not limited to, PEG-12 dimethicone, PEG/PPG-18/18 dimethicone, and PPG-12 dimethicone.

Other suitable platicizers include, but are not limited to, alkyl and allyl phthalates; napthalates; lactates (e.g., sodium, ammonium and potassium salts); sorb eth-30; urea; lactic acid; sodium pyrrolidone carboxylic acid (PCA); sodium hyraluronate or hyaluronic acid; soluble collagen; modified protein; monosodium L-glutamate; alpha & beta hydroxyl acids such as glycolic acid, lactic acid, citric acid, maleic acid and salicylic acid; glyceryl polymethacrylate; polymeric plasticizers such as polyquaterniums; proteins and amino acids such as glutamic acid, aspartic acid, and lysine; hydrogen starch hydrolysates; other low molecular weight esters (e.g., esters of $C_2$-$C_{10}$ alcohols and acids); and any other water soluble plasticizer known to one skilled in the art of the foods and plastics industries; and mixtures thereof.

Particularly preferred examples of plasticizers include glycerin, ethylene glycol, polyethyleneglycol, propylene glycol, and mixtures thereof. Most preferred plasticizer is glycerin. The presence of a preferred plasticizer, for example glycerin, in the solid sheet may additionally bring about anti-wrinkle benefit. Particularly, when the solid sheet article comprises a preferred amount of glycerin (e.g. from 22% to 40%, by total weight of the solid sheet), the anti-wrinkle effect may be even more significant.

3. Cationic Surfactant

The solid sheet article of the present invention article comprises one or more cationic surfactants. The cationic surfactant may function as a fabric care active for example a fabric conditioner and/or a fabric softener, a home care active, a hair care active, a beauty care active and/or a personal care active. Particularly, the solid sheet article may comprise from about 1% to about 50%, preferably from about 5% to about 45%, more preferably from about 10% to about 40%, most preferably from about 15% to about 35%, for example about 10%, about 15%, about 20%, about 25%, about 30%, about 35%, about 40% or any ranges therebetween, of the cationic surfactant by total weight of the solid sheet article. Correspondingly, the wet pre-mixture used for forming such solid sheet article may comprise from about 0.1% to about 40%, preferably from about 1% to about 35%, more preferably from about 5% to about 30%, yet more preferably from about 8% to about 35%, most preferably from about 10% to about 30%, for example about 10%, about 15%, about 20%, about 25%, about 30%, about 35%, about 40% or any ranges therebetween, of the cationic surfactant by weight of the wet pre-mixture.

Particularly, the cationic surfactant may be a quaternary ammonium compound and/or an amine compound. More particularly, the cationic surfactant may be selected from the group consisting of a diester quaternary ammonium (DEQA) compound, a mono-long alkyl quaternary ammonium compound, a di-long alkyl quaternary ammonium compound, a mono-long alkyl amine compound, and any combinations thereof. Yet more particularly, the cationic surfactant may be selected from the group consisting of alkyl trimethyl ammonium compound or amine precursors thereof, dialkyl dimethyl ammonium compound or amine precursors thereof, methyl-diethanolamine-based (MDEA-based) quaternary ammonium compound or amine precursors thereof, methyl-diisopropanolamine-based (MDIPA-based) quaternary ammonium compound or amine precursors thereof, triethanolamine-based (TEA-based) quaternary ammonium compound or amine precursors thereof and any combinations thereof. Most particularly, the cationic surfactant may be selected from the group consisting of behenyl trimethyl ammonium chloride; stearyl trimethyl ammonium chloride; cetyl trimethyl ammonium chloride; lauryl trimethyl ammonium chloride; hydrogenated tallow alkyl trimethyl ammonium chloride, dimethyl hydroxyethyl lauryl ammonium chloride, dialkyl (14-18) dimethyl ammonium chloride, ditallow alkyl dimethyl ammonium chloride, dihydrogenated tallow alkyl dimethyl ammonium chloride, distearyl dimethyl ammonium chloride, dicetyl dimethyl ammonium chloride, N,N-di(acyl-oxy ethyl)-N,N-dim ethyl ammonium chloride, N,N-di(acyl-oxyisopropyl)-N,N-dimethylammonium methylsulfate, N,N-di(acyl-oxyethyl)-N,N-methylhydroxyethylammonium methylsulfate and any combinations thereof. Exemplary cationic surfactants include diethyl ester dimethyl ammonium chloride (DEEDMAC), dipalmethyl hydroxyethylammoinum methosulfate, coconut trimethyl ammonium chloride and lauryl trimethyl ammonium chloride and the like.

Further, in an embodiment, the cationic surfactant may be formed from a reaction product of a fatty acid and an aminoalcohol obtaining mixtures of mono-, di-, and, in one embodiment, triester compounds. In another embodiment, the cationic surfactant comprises one or more softener quaternary ammonium compounds such, but not limited to, as a monoalkylquaternary ammonium compound, dialkyl-quaternary ammonium compound, a diamido quaternary compound, a diester quaternary ammonium compound, a monoester quaternary ammonium compound or a combination thereof.

Exemplary quaternary ammonium compounds include, but are not limited to, alkylated quaternary ammonium compounds, ring or cyclic quaternary ammonium compounds, aromatic quaternary ammonium compounds, diquaternary ammonium compounds, alkoxylated quaternary ammonium compounds, amidoamine quaternary ammonium compounds, ester quaternary ammonium compounds, and mixtures thereof. Examples of such compounds are described in U.S. Pat. No. 7,381,697, column 3, line 43—column 4, line 67; U.S. Pat. No. 7,135,451, column 5, line 1—column 11, line 40. See also U.S. Pat. Nos. 4,424, 134; 4,767,547; 5,545,340; 5,545,350; 5,562,849; and 5,574,179.

Preferably, the cationic surfactant may comprise compounds of the following formula:

$$\{R_{4-m}\text{—}N^+\text{—}[Z\text{—}Y\text{—}R^1]_m\}X^-$$

wherein each R comprises either hydrogen, a short chain $C_1$-$C_6$, in one aspect a $C_1$-$C_3$ alkyl or hydroxyalkyl group, for example methyl, ethyl, propyl, hydroxyethyl, and the like, poly($C_{2-3}$ alkoxy), polyethoxy, benzyl, or mixtures thereof; each Z is independently $(CH_2)n$, CH2-CH(CH3)- or CH—(CH3)-CH2-; each Y may comprise —O—(O)C—, —C(O)—O—, —NR—C(O)—, or —C(O)—NR—; each m is 2 or 3; each n is from 1 to about 4, in one aspect 2; the sum of carbons in each 10, plus one when Y is —O—(O)C— or —NR—C(O)—, may be $C_{12}$-$C_{22}$, or $C_{14}$-$C_{20}$, with each $R^1$ being a hydrocarbyl, or substituted hydrocarbyl group; and $X^-$ may comprise any compatible anion. In one aspect, the compatible anion may comprise chloride, bromide, methylsulfate, ethylsulfate, sulfate, and nitrate. In another aspect, the compatible anion may comprise chloride or methyl sulfate. As used herein, when the diester is specified, it can include the monoester that is present.

Particularly, suitable cationic surfactant may be reaction products of fatty acids with dialkylenetriamines in, e.g., a molecular ratio of about 2:1, the reaction products containing compounds of the formula:

$$R^1\text{—}C(O)\text{—}NH\text{—}R^2\text{—}NH\text{—}R^3\text{—}NH\text{—}C(O)\text{—}R^1$$

wherein $R^1$, $R^2$ are defined as above, and each $R^3$ is a $C_{1-6}$ alkylene group, preferably an ethylene group. Examples of these actives are reaction products of tallow acid, canola acid, or oleic acids with diethylenetriamine in a molecular ratio of about 2:1, the reaction product mixture containing N,N"-ditallowoyldiethylenetriamine, N,N"-dicanola-oyldiethylenetriamine, or N,N"-dioleoyldiethylenetriamine, respectively, with the formula:

$$R^1\text{—}C(O)\text{—}NH\text{—}CH_2CH_2\text{—}NH\text{—}CH_2CH_2\text{—}NH\text{—}C(O)\text{—}R^1$$

wherein $R^2$ and $R^3$ are divalent ethylene groups, $R^1$ is defined above and acceptable examples of this structure when $R^1$ is the oleoyl group of a commercially available oleic acid derived from a vegetable or animal source, include EMERSOL® 223LL or EMERSOL® 7021, available from Henkel Corporation.

Another suitable cationic surfactant may have the formula:

$$[R^1\text{—}C(O)\text{—}NR\text{—}R^2\text{—}N(R)_2\text{—}R^3\text{—}NR\text{—}C(O)\text{—}R^1]^+X^-$$

wherein R, $R^1$, $R^2$, $R^3$ and $X^-$ are defined as above. Examples of this active are the di-fatty amidoamines based softener having the formula:

$$[R^1\text{—}C(O)\text{—}NH\text{—}CH_2CH_2\text{—}N(CH_3)(CH_2CH_2OH)\text{—}CH_2CH_2\text{—}NH\text{—}C(O)\text{—}R^1]^+ CH_3SO_4^-$$

wherein $R^1$—C(O) is an oleoyl group, soft tallow group, or a hardened tallow group available commercially from Degussa under the trade names VARISOFT® 222LT, VARISOFT® 222, and VARISOFT® 110, respectively.

Another suitable cationic surfactant may have the general formula:

$$[R_3N^+CH_2CH(YR^1)(CH_2YR^1)]X^-$$

wherein each Y, R, $R^1$, and $X^-$ have the same meanings as before. An example of a preferred cationic surfactant is the "propyl" ester quaternary ammonium compound having the formula 1,2-di(acyloxy)-3-trimethylammoniopropane chloride.

Cationic surfactant useful herein can be one cationic surfactant or a mixture of two or more cationic surfactants. Preferably, the cationic surfactant may be selected from the group consisting of: a mono-long alkyl quaternized ammonium salt; a combination of a mono-long alkyl quaternized ammonium salt and a di-long alkyl quaternized ammonium salt; a mono-long alkyl amine; a combination of a mono-long alkyl amine and a di-long alkyl quaternized ammonium salt; and a combination of a mono-long alkyl amine and a mono-long alkyl quaternized ammonium salt.

Mono-long alkyl amine useful herein are those having one long alkyl chain of preferably from 12 to 30 carbon atoms, more preferably from 16 to 24 carbon atoms, still more preferably from 18 to 22 alkyl group. Mono-long alkyl amines useful herein also include mono-long alkyl amidoamines. Primary, secondary, and tertiary fatty amines are useful.

Particularly useful are tertiary amido amines having an alkyl group of from about 12 to about 22 carbons. Exemplary tertiary amido amines include: stearamidopropyldimethylamine, stearamidopropyldiethylamine, stearamidoethyldiethylamine, stearamidoethyldimethylamine, palmitamidopropyldimethylamine, palmitamidopropyldiethylamine, palmitamidoethyldiethylamine, palmitamidoethyldimethylamine, b ehenamidopropyldimethylamine, behenamidopropyldiethylamine, b ehenamidoethyldiethylamine, behenamidoethyldimethylamine, arachidamidopropyldimethylamine, arachidamidopropyldiethylamine, arachidamidoethyldiethylamine, arachidamidoethyldimethylamine, diethylaminoethylstearamide. Useful amines in the present invention are disclosed in U.S. Pat. No. 4,275,055, Nachtigal, et al.

These amines may be used in combination with acids such as l-glutamic acid, lactic acid, hydrochloric acid, malic acid, succinic acid, acetic acid, fumaric acid, tartaric acid, citric acid, l-glutamic hydrochloride, maleic acid, and mixtures thereof; more preferably l-glutamic acid, lactic acid, citric acid, at a molar ratio of the amine to the acid of from about 1:0.3 to about 1:2, more preferably from about 1:0.4 to about 1:1.

The mono-long alkyl quaternized ammonium salts useful herein are those having one long alkyl chain which has from 12 to 30 carbon atoms, preferably from 16 to 24 carbon atoms, more preferably C18-22 alkyl group. The remaining groups attached to nitrogen are independently selected from an alkyl group of from 1 to about 4 carbon atoms or an alkoxy, polyoxyalkylene, alkylamido, hydroxyalkyl, aryl or alkylaryl group having up to about 4 carbon atoms.

Mono-long alkyl quaternized ammonium salts useful herein are those having the following formula:

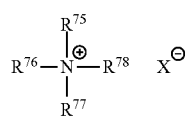

wherein one of $R^{75}$, $R^{76}$, $R^{77}$ and $R^{78}$ is selected from an alkyl group of from 12 to 30 carbon atoms or an aromatic, alkoxy, polyoxyalkylene, alkylamido, hydroxyalkyl, aryl or alkylaryl group having up to about 30 carbon atoms; the remainder of $R^{75}$, $R^{76}$, $R^{77}$ and $R^{78}$ are independently selected from an alkyl group of from 1 to about 4 carbon atoms or an alkoxy, polyoxyalkylene, alkylamido, hydroxyalkyl, aryl or alkylaryl group having up to about 4 carbon atoms; and X⁻ is a salt-forming anion such as those selected from halogen, (e.g. chloride, bromide), acetate, citrate, lactate, glycolate, phosphate, nitrate, sulfonate, sulfate, alkylsulfate, and alkyl sulfonate radicals. The alkyl groups can contain, in addition to carbon and hydrogen atoms, ether and/or ester linkages, and other groups such as amino groups. The longer chain alkyl groups, e.g., those of about 12 carbons, or higher, can be saturated or unsaturated. Preferably, one of $R^{75}$, $R^{76}$, $R^{77}$ and $R^{78}$ is selected from an alkyl group of from 12 to 30 carbon atoms, more preferably from 16 to 24 carbon atoms, still more preferably from 18 to 22 carbon atoms, even more preferably 22 carbon atoms; the remainder of $R^{75}$, $R^{76}$, $R^{77}$ and $R^{78}$ are independently selected from $CH_3$, $C_2H_5$, $C_2H_4OH$, and mixtures thereof; and X is selected from the group consisting of Cl, Br, $CH_3O$ $SO_3$, $C_2H_5O$ $SO_3$, and mixtures thereof.

Nonlimiting examples of such mono-long alkyl quaternized ammonium salt cationic surfactants include: behenyl trimethyl ammonium salt; stearyl trimethyl ammonium salt; cetyl trimethyl ammonium salt; and hydrogenated tallow alkyl trimethyl ammonium salt.

When used, di-long alkyl quaternized ammonium salts may be preferably combined with a mono-long alkyl quaternized ammonium salt and/or mono-long alkyl amine salt, at the weight ratio of from 1:1 to 1:5, more preferably from 1:1.2 to 1:5, still more preferably from 1:1.5 to 1:4, in view of stability in rheology and conditioning benefits.

Di-long alkyl quaternized ammonium salts useful herein are those having two long alkyl chains of from 12 to 30 carbon atoms, more preferably from 16 to 24 carbon atoms, still more preferably from 18 to 22 carbon atoms. Such di-long alkyl quaternized ammonium salts useful herein are those having the following formula:

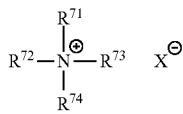

wherein two of $R^{71}$, $R^{72}$, $R^{73}$ and $R^{74}$ are selected from an aliphatic group of from 12 to 30 carbon atoms, preferably from 16 to 24 carbon atoms, more preferably from 18 to 22 carbon atoms or an aromatic, alkoxy, polyoxyalkylene, alkylamido, hydroxyalkyl, aryl or alkylaryl group having up to about 30 carbon atoms; the remainder of $R^{71}$, $R^{72}$, $R^{73}$ and $R^{74}$ are independently selected from an aliphatic group of from 1 to about 8 carbon atoms, preferably from 1 to 3 carbon atoms or an aromatic, alkoxy, polyoxyalkylene, alkylamido, hydroxyalkyl, aryl or alkylaryl group having up to about 8 carbon atoms; and X⁻ is a salt-forming anion selected from the group consisting of halides such as chloride and bromide, C1-C4 alkyl sulfate such as methosulfate and ethosulfate, and mixtures thereof. The aliphatic groups can contain, in addition to carbon and hydrogen atoms, ether linkages, and other groups such as amino groups. The longer chain aliphatic groups, e.g., those of about 16 carbons, or higher, can be saturated or unsaturated. Preferably, two of $R^{71}$, $R^{72}$, $R^{73}$ and $R^{74}$ are selected from an alkyl group of from 12 to 30 carbon atoms, preferably from 16 to 24 carbon atoms, more preferably from 18 to 22 carbon atoms; and the remainder of $R^{71}$, $R^{72}$, $R^{73}$ and $R^{74}$ are independently selected from $CH_3$, $C_2H_5$, $C_2H_4OH$, $CH_2C_6H_5$, and mixtures thereof.

Such preferred di-long alkyl cationic surfactants include, for example, dialkyl (14-18) dimethyl ammonium chloride, ditallow alkyl dimethyl ammonium chloride, dihydrogenated tallow alkyl dimethyl ammonium chloride, distearyl dimethyl ammonium chloride, and dicetyl dimethyl ammonium chloride.

4. Additional Ingredients

In addition to the above-described ingredients, e.g., the water-soluble polymer, the plasticizer and the cationic surfactant, the solid sheet article may comprise one or more additional ingredients, depending on its intended application. Particularly, the additional ingredients may be present in the solid sheets and/or the coating composition. Such one or more additional ingredients may be selected from the group consisting of additional surfactants; perfumes (including encapsulated perfumes or perfume microcapsules), silicone, an emulsifier, solvents (e.g. linear or branched lower $C_1$-$C_8$ alcohols, diols, glycerols or glycols; lower amine solvents such as $C_1$-$C_4$ alkanolamines, and mixtures thereof; more specifically 1,2-propanediol, ethanol, glycerol, monoethanolamine and triethanolamine), carriers, hydrotropes, builders, chelants, dispersants, enzymes and enzyme stabilizers, catalytic materials, bleaches (including photobleaches) and bleach activators, colorants (such as pigments and dyes, including hueing dyes), brighteners, dye transfer inhibiting agents, clay soil removal/anti-redeposition agents, structurants, rheology modifiers, suds suppressors, processing aids, anti-microbial agents, a non-film forming polymer, an antifoamer, a defoamer, and the like.

Additional Surfactants

Additional surfactants suitable for use in the solid sheet article include anionic surfactants, nonionic surfactants, zwitterionic surfactants, amphoteric surfactants, or combinations thereof. The one or more additional surfactants may be present from about 0% to about 25%, preferably from about 0% to about 15%, for example about 0.1%, about 1%, about 3%, about 5%, about 7%, about 10% or any ranges therebetween, by total weight of the solid sheet article. Additional surfactants may be present in the solid sheets, the coating composition between the solid sheets or both.

Non-limiting examples of anionic surfactants suitable for use herein include alkyl and alkyl ether sulfates, sulfated monoglycerides, sulfonated olefins, alkyl aryl sulfonates, primary or secondary alkane sulfonates, alkyl sulfosuccinates, acyl taurates, acyl isethionates, alkyl glycerylether sulfonate, sulfonated methyl esters, sulfonated fatty acids, alkyl phosphates, acyl glutamates, acyl sarcosinates, alkyl sulfoacetates, acylated peptides, alkyl ether carboxylates, acyl lactylates, anionic fluorosurfactants, sodium lauroyl glutamate, and combinations thereof. Particularly, suitable anionic surfactants include $C_6$-$C_{20}$ linear alkylbenzene sulphonates (LAS); sodium trideceth sulfates (STS) having a weight average degree of alkoxylation ranging from about 0.5 to about 5; unalkoxylated $C_6$-$C_{20}$ linear or branched alkyl sulfates; $C_6$-$C_{20}$ linear or branched alkylalkoxy sulfates (AAS); water-soluble salts of the organic, sulfuric acid reaction products of the general formula [$R^1$—$SO_3$-M], wherein $R^1$ is chosen from the group consisting of a straight or branched chain, saturated aliphatic hydrocarbon radical having from about 6 to about 20, preferably about 10 to about 18, carbon atoms; and M is a cation; β-alkyloxy alkane sulfonates.

Non-limiting examples of nonionic surfactants suitable for use herein including but not limited to: alkyl alkoxylated alcohols, alkyl alkoxylated phenols, alkyl polysaccharides (especially alkyl glucosides and alkyl polyglucosides), polyhydroxy fatty acid amides, alkoxylated fatty acid esters, sucrose esters, sorbitan esters and alkoxylated derivatives of sorbitan esters, amine oxides, and the like. Preferred non-ionic surfactants are those of the formula $R^1(OC_2H_4)$—OH, wherein $R^1$ is a $C_8$-$C_{18}$ alkyl group or alkyl phenyl group, and n is from about 1 to about 80. Particularly preferred are $C_8$-$C_{18}$ alkyl ethoxylated alcohols having a weight average degree of ethoxylation from about 1 to about 20, preferably from about 5 to about 15, more preferably from about 7 to about 10, such as NEODOL® nonionic surfactants commercially available from Shell. Other non-limiting examples of nonionic surfactants useful herein include: $C_6$-$C_{12}$ alkyl phenol alkoxylates where the alkoxylate units may be ethyleneoxy units, propyleneoxy units, or a mixture thereof; $C_{12}$-$C_{18}$ alcohol and $C_6$-$C_{12}$ alkyl phenol condensates with ethylene oxide/propylene oxide block polymers such as Pluronic® from BASF; $C_{14}$-$C_{22}$ mid-chain branched alcohols (BA); $C_{14}$-$C_{22}$ mid-chain branched alkyl alkoxylates, $BAE_x$, wherein x is from 1 to 30; alkyl polysaccharides, specifically alkyl polyglycosides; Polyhydroxy fatty acid amides; and ether capped poly(oxyalkylated) alcohol surfactants. Suitable nonionic surfactants also include those sold under the tradename Lutensol® from BASF. In a preferred embodiment, the nonionic surfactant is selected from sorbitan esters and alkoxylated derivatives of sorbitan esters including sorbitan monolaurate (SPAN® 20), sorbitan monopalmitate (SPAN® 40), sorbitan monostearate (SPAN® 60), sorbitan tristearate (SPAN® 65), sorbitan monooleate (SPAN® 80), sorbitan trioleate (SPAN® 85), sorbitan isostearate, polyoxyethylene (20) sorbitan monolaurate (Tween® 20), polyoxyethylene (20) sorbitan monopalmitate (Tween® 40), polyoxyethylene (20) sorbitan monostearate (Tween® 60), polyoxyethylene (20) sorbitan monooleate (Tween® 80), polyoxyethylene (4) sorbitan monolaurate (Tween® 21), polyoxyethylene (4) sorbitan monostearate (Tween® 61), polyoxyethylene (5) sorbitan monooleate (Tween® 81), all available from Uniqema, and combinations thereof.

The most preferred nonionic surfactants for practice of the present invention include $C_6$-$C_{20}$ linear or branched alkyl-alkoxylated alcohols (AA) having a weight average degree of alkoxylation ranging from 5 to 15, more preferably $C_{12}$-$C_{14}$ linear ethoxylated alcohols having a weight average degree of alkoxylation ranging from 7 to 9, for example AE7 and AE9.

Surprisingly, the presence of non-ionic surfactant in the solid sheet may bring about improved dissolution profile. In a preferred but not necessary embodiment, the solid sheet article may comprise from about 0.01% to about 20%, preferably from about 0.1% to about 12%, more preferably from about 0.5% to about 8%, most preferably from about 1% to about 5%, for example about 0.01%, about 0.1%, about 1%, about 2%, about 3%, about 4%, about 5%, about 6%, about 7%, about 8%, about 10%, about 12%, about 15% or any ranges therebetween, of a non-ionic surfactant by total weight of the solid sheet article. Further, it has been discovered by the inventors of the present invention that, when the amount of the non-ionic surfactant is too high (for example, more than about 10%, 7% or 5%), it may compromise the function of the cationic surfactant (for example, as a fabric softener) to some extent. As such, a perfect balance between the improved dissolution and the function of the cationic surfactant might be achieved when a non-ionic surfactant is presence in a most preferred range of amount, for example from about 1% to about 5%.

Amphoteric surfactants suitable for use in the solid sheet article of the present invention includes those that are broadly described as derivatives of aliphatic secondary and tertiary amines in which the aliphatic radical can be straight or branched chain and wherein one of the aliphatic substituents contains from about 8 to about 18 carbon atoms and one contains an anionic water solubilizing group, e.g., carboxy, sulfonate, sulfate, phosphate, or phosphonate. Examples of compounds falling within this definition are sodium 3-dodecyl-aminopropionate, sodium 3-dodecylaminopropane sulfonate, sodium lauryl sarcosinate, N-alkyltaurines such as the one prepared by reacting dodecylamine with sodium isethionate, and N-higher alkyl aspartic acids.

Zwitterionic surfactants suitable include those that are broadly described as derivatives of aliphatic quaternary ammonium, phosphonium, and sulfonium compounds, in which the aliphatic radicals can be straight or branched chain, and wherein one of the aliphatic substituents contains from about 8 to about 18 carbon atoms and one contains an anionic group, e.g., carboxy, sulfonate, sulfate, phosphate, or phosphonate. Such suitable zwitterionic surfactants can be represented by the formula:

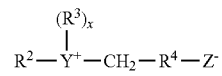

wherein $R^2$ contains an alkyl, alkenyl, or hydroxy alkyl radical of from about 8 to about 18 carbon atoms, from 0 to about 10 ethylene oxide moieties and from 0 to about 1 glyceryl moiety; Y is selected from the group consisting of nitrogen, phosphorus, and sulfur atoms; $R^3$ is an alkyl or monohydroxyalkyl group containing about 1 to about 3 carbon atoms; X is 1 when Y is a sulfur atom, and 2 when Y is a nitrogen or phosphorus atom; $R^4$ is an alkylene or hydroxyalkylene of from about 1 to about 4 carbon atoms and Z is a radical selected from the group consisting of carboxylate, sulfonate, sulfate, phosphonate, and phosphate groups.

In some embodiments, the additional surfactant may be selected from the group consisting of: a $C_6$-$C_{20}$ linear alkylbenzene sulfonate (LAS), a $C_6$-$C_{20}$ linear or branched alkylalkoxy sulfates (AAS) having a weight average degree of alkoxylation ranging from 0.5 to 10, a $C_6$-$C_{20}$ linear or branched alkylalkoxylated alcohols (AA) having a weight average degree of alkoxylation ranging from 5 to 15, a $C_6$-$C_{20}$ linear or branched alkyl sulfates (AS), alkyl sulfates, alkyl ether sulfates, alkylamphoacetates and any combinations thereof.

Perfume

The solid sheet article of the present invention may comprise a perfume. Preferably, the solid sheet article may comprise from about 0.01% to about 50%, preferably from about 0.02% to about 30%, more preferably from about 0.1% to about 20%, for example about 0.01%, about 0.02%, about 0.05%, about 0.1%, about 0.2%, about 0.3%, about 0.5%, about 1%, about 2%, about 3%, about 5%, about 10% or any ranges therebetween, of a perfume, by total weight of the solid sheet article.

Particularly, the perfume may be present in the solid sheets and/or the coating composition. Preferably, the perfume may be free perfumes, perfume microcapsules, or any combinations thereof. Particularly, the coating composition may comprise from 1% to 99%, preferably from 5% to 90%, more preferably from 10% to 80%, for example 1%, 2%, 3%, 4%, 5%, 8%, 10%, 15%, 20%, 25%, 30%, 35%, 40%, 45%, 50%, 55%, 60%, 65%, 70%, 75%, 80%, 85%, 90%, 95% or any ranges therebetween, of the perfume by total weight of the coating composition.

In some embodiments, at least 50%, preferably at least 70%, more preferably at least 90%, most preferably at least 99%, of perfume in the solid article according to the present disclosure is present in the coating composition. It may bring about improved performance of perfumes, for example longevity, perfume stability, deposition or release benefit.

Silicone

The solid sheet article of the present invention may comprise a silicone, preferably organosilicones. Preferably, the solid sheet article may comprise from about 0.01% to about 50%, preferably from about 0.1% to about 30%, more preferably from about 1% to about 20%, for example about 1%, about 2%, about 3%, about 5%, about 7%, about 10%, about 15%, about 20% or any ranges therebetween, of a silicone, by total weight of the solid sheet article. When the solid sheet article of the present invention is used as a fabric conditioning product, silicone may function as a co-softener.

Particularly, the silicone may be present in the solid sheets and/or the coating composition. Preferably, the coating composition may comprise from about 0.01% to about 100%, preferably from about 0.1% to about 99.9%, more preferably from about 1% to about 99%, for example about 1%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95% or any ranges therebetween, of a silicone, by total weight of the coating composition.

Particularly, suitable organosilicones may comprise Si—O moieties and may be selected from (a) non-functionalized siloxane polymers, (b) functionalized siloxane polymers, and mixtures thereof. The molecular weight of the organosilicone is usually indicated by the reference to the viscosity of the material. In one aspect, the organosilicones may comprise a viscosity of from about 10 to about 2,000,000 centistokes at 25° C. In another aspect, suitable organosilicones may have a viscosity of from about 10 to about 800,000 centistokes at 25° C.

Suitable organosilicones may be linear, branched or cross-linked and suitable examples are described in U.S. Pat. Nos. 6,815,069; 7,153,924; 7,321,019; and 7,427, 648; and U.S. Patent Application 61/319,939.

In some embodiments, the silicone may be selected from the group consisting of vinyl dimethicone/methicone silsesquioxane crosspolymer, poly silicone, polymethylsilsesquioxane, diphenyl dimethicone/vinyl diphenyl dimethicone/silsesquioxane crosspolymer, and any combinations thereof.

Solvents

Other optional components in the solid sheet article may include solvents, especially water miscible solvents and co-solvents useful as solublizing agents for polymeric structurants and as drying accelerators. Particularly, the solvent may be present in the solid sheets and/or the coating composition. Non-limiting examples of suitable solvents include alcohols, esters, ketones, aromatic hydrocarbons, aliphatic hydrocarbons, ethers, and combinations thereof. Alcohols and esters are more preferred. Preferred alcohols are monohydric. The most preferred monohydric alcohols are ethanol, iso-propanol, and n-propanol. The most preferred esters are ethyl acetate and butyl acetate. Other non-limiting examples of suitable organic solvents are benzyl alcohol, amyl acetate, propyl acetate, acetone, heptane, iso-butyl acetate, iso-propyl acetate, toluene, methyl acetate, iso-butanol, n-amyl alcohol, n-butyl alcohol, hexane, and methyl ethyl ketone. methanol, ethanol, n-propanol, isopropanol, n-butanol, isobutanol, methylethylketone, acetone, and combinations thereof.

In some embodiments, the solvent may be selected from the group consisting of glycerol, propylene glycol, 1,3-propanediol, diethylene glycol, dipropylene glycol, ethanolamine, ethanol, water and any combinations thereof.

Deposition Aid

In one aspect, the solid sheet article may comprise from about 0.01% to about 20%, from about 0.1 to about 15%, or from about 0.2 to about 10% of a deposition aid, by total weight of the solid sheet article. Particularly, the deposition aid may be present in the solid sheets and/or the coating composition. Suitable deposition aids are disclosed in, for example, US Pat. App. Pub. No. 2008/0242584.

In one aspect, the deposition aid may be a cationic or amphoteric polymer. In one aspect, the deposition aid may be a cationic polymer. Cationic polymers in general and their method of manufacture are known in the literature. In one aspect, the cationic polymer may have a cationic charge density of from about 0.005 to about 23, from about 0.01 to about 12, or from about 0.1 to about 7 milliequivalents/g, at the pH of intended use of the composition. For amine-containing polymers, wherein the charge density depends on the pH of the composition, charge density is measured at the intended use pH of the product. Such pH will generally range from about 2 to about 11, more generally from about 2.5 to about 9.5. Charge density is calculated by dividing the number of net charges per repeating unit by the molecular weight of the repeating unit. The positive charges may be located on the backbone of the polymers and/or the side chains of polymers. Particularly, the cationic polymer may be cationic hydroxyethyl cellulose, preferably having a weight average molecular weight of from 200 kDa to 600 kDa (e.g. 400 kDa), a charge density of from 0.1 to 0.3 (e.g. 0.18), and/or an average weight percent of nitrogen per anhydroglucose repeat unit of from 0.2% to 0.4% (e.g. 0.28%).

One group of suitable cationic polymers includes those produced by polymerization of ethylenically unsaturated monomers using a suitable initiator or catalyst, such as those disclosed in WO 00/56849 and U.S. Pat. No. 6,642,200.

Additional Adjunct Ingredients

In another embodiment, the solid sheet article may further comprise additional adjunct ingredients. Particularly, the additional adjunct ingredients may be present in the solid sheets and/or the coating composition. These additional adjunct ingredients can act as an processing aids and modify properties of the solid sheet article such as solubility and rate of dissolution, dissolution stability, resistance to moisture pickup from humidity in storage, stretchability, feel, brittleness, and texture of the substrate, appearance and shine, and ease and speed of processing, casting extruding, or drying the substrate, mechanical handling of the article, and storage of the article. Such additional adjunct ingredients include emulsifiers, non-film forming polymers, anti-block agents, antifoamers, defoamers, biocides, preservatives, colorants, opacifiers, pearlescing agents, fillers and bulking agents, a rheology modifier and the like.

The rheology modifier may be preferably selected from the group consisting of: cellulose and derivatives; a guar and guar derivatives; polyethylene oxide, polypropylene oxide, and POE-PPO copolymers; polyvinylpyrrolidone, cross-linked polyvinylpyrrolidone and derivatives; polyvinylalcohol and derivatives; polyethyleneimine and derivatives;

inorganic particles such sodium carbonate and sodium sulphate; silicon dioxide; water-swellable clays; gums; and any combinations thereof.

The emulsifier may be selected from the group consisting of mono- and di-glycerides, fatty alcohols, polyglycerol esters, propylene glycol esters, sorbitan esters, polyhydroxystearic acid and any combinations thereof.

The solid sheet article of the present invention may further comprise other optional ingredients that are known for use or otherwise useful in compositions, provided that such optional materials are compatible with the selected essential materials described herein, or do not otherwise unduly impair product performance.

III. Processes for Making Solid Sheets

The process for making a flexible, porous, dissolvable solid sheet article comprising a water-soluble polymer, a plasticizer and a cationic surfactant may comprise the steps of: a) preparing a wet pre-mixture comprising the water-soluble polymer, the plasticizer and the cationic surfactant, wherein the weight ratio of the plasticizer over the cationic surfactant is from about 0.9 to about 2; b) aerating the wet pre-mixture to form an aerated wet pre-mixture; c) forming the aerated wet pre-mixture into a sheet having opposing first and second sides; and d) drying the formed sheet to make the sheet article.

Particularly, aeration of the wet pre-mixture is conducted in order to introduce a sufficient amount of air bubbles into the wet pre-mixture for subsequent formation of the OCF structures therein upon drying. Once sufficiently aerated, the wet pre-mixture is characterized by a density that is significantly lower than that of the non-aerated wet pre-mixture (which may contain a few inadvertently trapped air bubbles) or an insufficiently aerated wet pre-mixture (which may contain some bubbles but at a much lower volume percentage and of significantly larger bubble sizes). Preferably, the aerated wet pre-mixture has a density ranging from about 0.1 g/ml to about 0.7 g/ml, preferably from about 0.15 g/ml to about 0.6 g/ml, more preferably from about 0.2 g/ml to about 0.5 g/ml, most preferably from about 0.25 g/ml to about 0.45 g/ml.

Aeration can be accomplished by either physical or chemical means in the present invention. In one embodiment, it can be accomplished by introducing a gas into the wet premixture through mechanical agitation, for example, by using any suitable mechanical processing means, including but not limited to: a rotor stator mixer, a planetary mixer, a pressurized mixer, a non-pressurized mixer, a batch mixer, a continuous mixer, a semi-continuous mixer, a high shear mixer, a low shear mixer, a submerged sparger, or any combinations thereof. In another embodiment, it may be achieved via chemical means, for example, by using chemical foaming agents to provide in-situ gas formation via chemical reaction of one or more ingredients, including formation of carbon dioxide ($CO_2$ gas) by an effervescent system. In a particularly preferred embodiment, it has been discovered that the aeration of the wet pre-mixture can be cost-effectively achieved by using a continuous pressurized aerator or mixer that is conventionally utilized in the foods industry in the production of marshmallows WO2010077627 discloses a batch process for forming porous sheets with open-celled foam (OCF) structures characterized by a Percent Open Cell Content of from about 80% to 100%, which functions to improve dissolution. Specifically, a pre-mixture of raw materials is first formed, which is vigorously aerated and then heat-dried in batches (e.g., in a convection oven or a microwave oven) to form the porous sheets with the desired OCF structures. Although such OCF structures significantly improve the dissolution rate of the resulting porous sheets, there is still a visibly denser and less porous bottom region with thicker cell walls in such sheets. Such high-density bottom region may negatively impact the flow of water through the sheets and thereby may adversely affect the overall dissolution rate of the sheets. When a plurality of such sheets is stacked together to form a multilayer structure, the "barrier" effect of multiple high-density bottom regions is especially augmented.

WO2012138820 discloses a similar process as that of WO2010077627, except that continuous drying of the aerated wet pre-mixture is achieved by using, e.g., an impingement oven (instead of a convection oven or a microwave oven). The OCF sheets formed by such a continuous drying process are characterized by improved uniformity/consistency in the pore structures across different regions thereof. Unfortunately, there are still rate-limiting factors in such OCF sheets, such as a top surface with relatively smaller pore openings and a top region with relatively smaller pores (i.e., a crust-like top region), which may negatively impact the flow of water therethrough and slow down the dissolution thereof.

During the drying step in the above-described processes, the OCF structures are formed under simultaneous mechanisms of water evaporation, bubble collapse, interstitial liquid drainage from the thin film bubble facings into the plateau borders between the bubbles (which generates openings between the bubbles and forms the open cells), and solidification of the pre-mixture. Various processing conditions may influence these mechanisms, e.g., solid content in the wet pre-mixture, viscosity of the wet pre-mixture, gravity, and the drying temperature, and the need to balance such processing conditions so as to achieve controlled drainage and form the desired OCF structures.

It has been a surprising and unexpected discovery that the direction of thermal energy employed (i.e., the heating direction) during the drying step may also have a significant impact on the resulting OCF structures, in addition to the above-mentioned processing conditions.

For example, if the thermal energy is applied in a non-directional matter (i.e., there is no clear heating direction) during the drying step, or if the heating direction is substantially aligned with the gravitational direction (i.e., with an offset angle of less than 90° in between) during most of the drying step, the resulting flexible, porous, dissolvable solid sheet tends to have a top surface with smaller pore openings and greater pore size variations in different regions along the direction across its thickness. In contrast, when the heating direction is offset from the gravitation direction (i.e., with an offset angle of 90° or more therebetween) during most of the drying step, the resulting solid sheet may have a top surface with larger pore openings and reduced pore size variations in different regions along the direction across the thickness of such sheet. Correspondingly, the latter sheets are more receptive to water flowing through and are therefore more dissolvable than the former sheets.

While not being bound by any theory, it is believed that the alignment or misalignment between the heating direction and the gravitational direction during the drying step and the duration thereof may significantly affect the interstitial liquid drainage between the bubbles, and correspondingly impacting the pore expansion and pore opening in the solidifying pre-mixture and resulting in solid sheets with very different OCF structures. Such differences are illustrated more clearly by FIGS. 1-4 hereinafter.

FIG. 1 shows a convection-based heating/drying arrangement. During the drying step, a mold 10 (which can be made of any suitable materials, such as metal, ceramic or Teflon®) is filled with an aerated wet pre-mixture, which forms a sheet 12 having a first side 12A (i.e., the top side) and an opposing second side 12B (i.e., the bottom side since it is in direct contact with a supporting surface of the mold 10). Such mold 10 is placed in a 130° C. convection oven for approximately 45-46 minutes during the drying step. The convection oven heats the sheet 12 from above, i.e., along a downward heating direction (as shown by the cross-hatched arrowhead), which forms a temperature gradient in the sheet 12 that decreases from the first side 12A to the opposing second side 12B. The downward heating direction is aligned with gravitational direction (as shown by the white arrowhead), and such an aligned position is maintained throughout the entire drying time. During drying, gravity drains the liquid pre-mixture downward toward the bottom region, while the downward heating direction dries the top region first and the bottom region last. As a result, a porous solid sheet is formed with a top surface that contains numerous pores with small openings formed by gas bubbles that have not had the chance to fully expand. Such a top surface with smaller pore openings is not optimal for water ingress into the sheet, which may limit the dissolution rate of the sheet. On the other hand, the bottom region of such sheet is dense and less porous, with larger pores that are formed by fully expanded gas bubbles, but which are very few in numbers, and the cell walls between the pores in such bottom region are thick due to the downward liquid drainage effectuated by gravity. Such a dense bottom region with fewer pores and thick cell walls is a further rate-limiting factor for the overall dissolution rate of the sheet.

Figure 2:
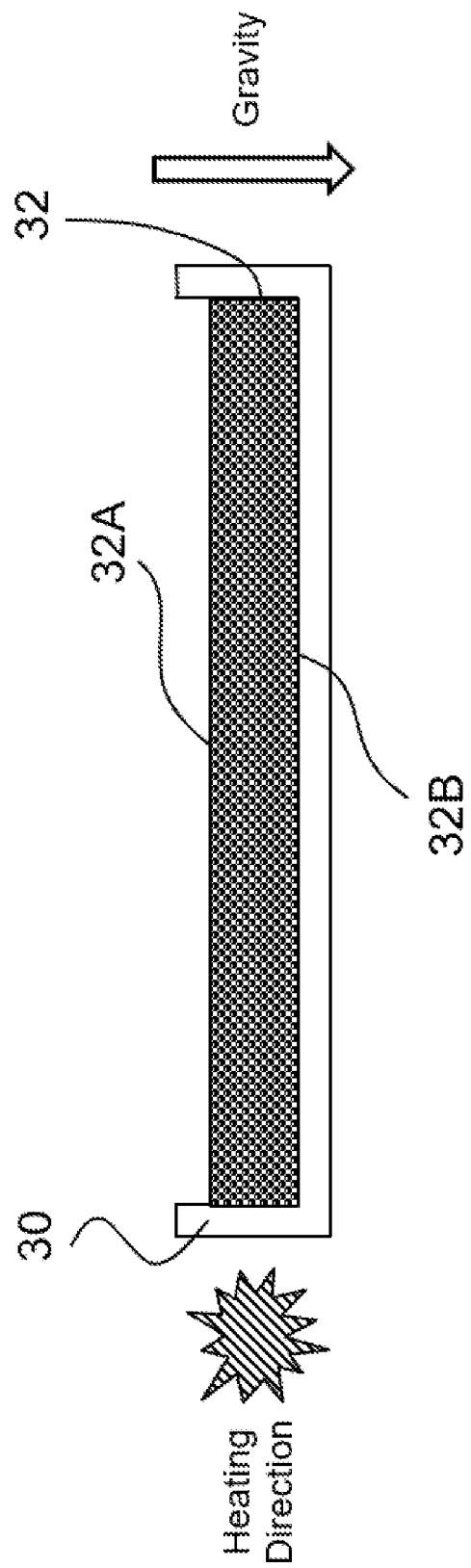
FIG. 2 shows a microwave-based heating/drying arrangement for making a flexible, porous, dissolvable solid sheet article in a batch process.

FIG. 2 shows a microwave-based heating/drying arrangement. During the drying step, a mold 30 is filled with an aerated wet pre-mixture, which forms a sheet 32 having a first side 32A (the top side) and an opposing second side 32B (the bottom side). Such mold 30 is then placed in a low energy density microwave applicator (not shown), which is provided by Industrial Microwave System Inc., North Carolina and operated at a power of 2.0 kW, a belt speed of 1 foot per minute and a surrounding air temperature of 54.4° C. The mold 30 is placed in such microwave application for approximately 12 minutes during the drying step. Such microwave applicator heats the sheet 32 from within, without any clear or consistent heating direction. Correspondingly, no temperature gradient is formed in the sheet 32. During drying, the entire sheet 32 is simultaneously heated, or nearly simultaneously heated, although gravity (as shown by the white arrowhead) still drains the liquid pre-mixture downward toward the bottom region. As a result, the solidified sheet so formed has more uniformly distributed and more evenly sized pores, in comparison with sheet formed by the convection-based heating/drying arrangement. However, the liquid drainage under gravity force during the microwave-based drying step may still result in a dense bottom region with thick cell walls. Further, simultaneous heating of the entire sheet 32 may still limit the pore expansion and pore opening on the top surface during the drying step, and the resulting sheet may still have a top surface with relatively smaller pore openings. Further, the microwave energy heats water within the sheet 32 and causes such water to boil, which may generate bubbles of irregular sizes and form unintended dense regions with thick cell walls.

Figure 3:
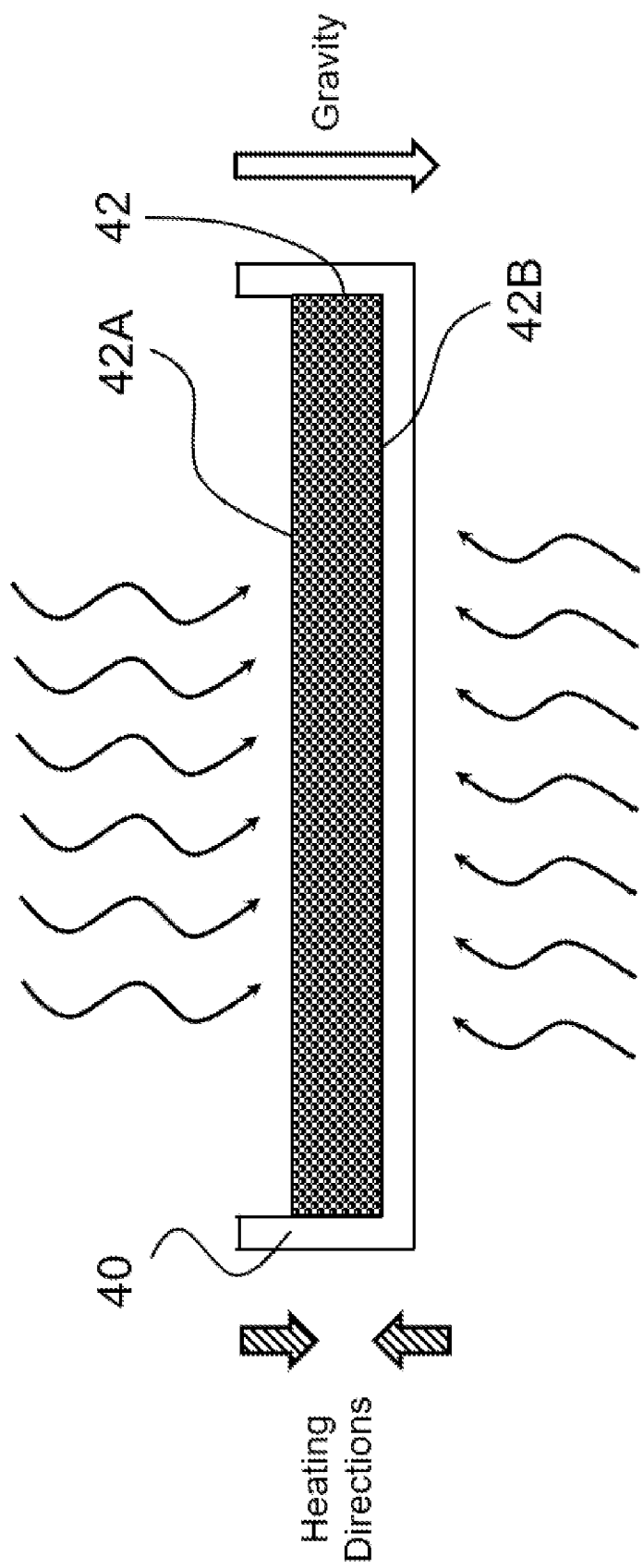
FIG. 3 shows an impingement oven-based heating/drying arrangement for making a flexible, porous dissolvable solid sheet article in a continuous process.

FIG. 3 shows an impingement oven-based heating/drying arrangement. During the drying step, a mold 40 is filled with an aerated wet pre-mixture, which forms a sheet 42 having a first side 42A (the top side) and an opposing second side 42B (the bottom side). Such mold 40 is then placed in a continuous impingement oven (not shown) under conditions similar to those described in Example 1, Table 2 of WO2012138820. Such continuous impingement oven heats the sheet 42 from both top and bottom at opposing and offsetting heating directions (shown by the two cross-hatched arrowheads). Correspondingly, no clear temperature gradient is formed in the sheet 42 during drying, and the entire sheet 42 is nearly simultaneously heated from both its top and bottom surfaces. Similar to the microwave-based heating/drying arrangement described in FIG. 3, gravity (as shown by the white arrowhead) continues to drain the liquid pre-mixture downward toward the bottom region in such impingement oven-based heating/drying arrangement of FIG. 4. As a result, the solidified sheet so formed has more uniformly distributed and more evenly sized pores, in comparison with sheet formed by the convection-based heating/drying arrangement. However, the liquid drainage under gravity force during the drying step may still result in a dense bottom region with thick cell walls. Further, nearly simultaneous heating of the sheet 42 from both the may still limit the pore expansion and pore opening on the top surface during the drying step, and the resulting sheet may still have a top surface with relatively smaller pore openings.

In addition to the above-described heating/drying arrangements (convection-based, microwave-based or impingement oven-based), the present invention provides another heating/drying arrangement for drying the aerated wet pre-mixture, in which the direction of heating is purposefully configured to counteract/reduce liquid drainage caused by the gravitational force toward the bottom region (thereby reducing the density and improving pore structures in the bottom region) and to allow more time for the air bubbles near the top surface to expand during drying (thereby forming significantly larger pore openings on the top surface of the resulting sheet). Both features function to improve overall dissolution rate of the sheet and are therefore desirable.

Figure 4:
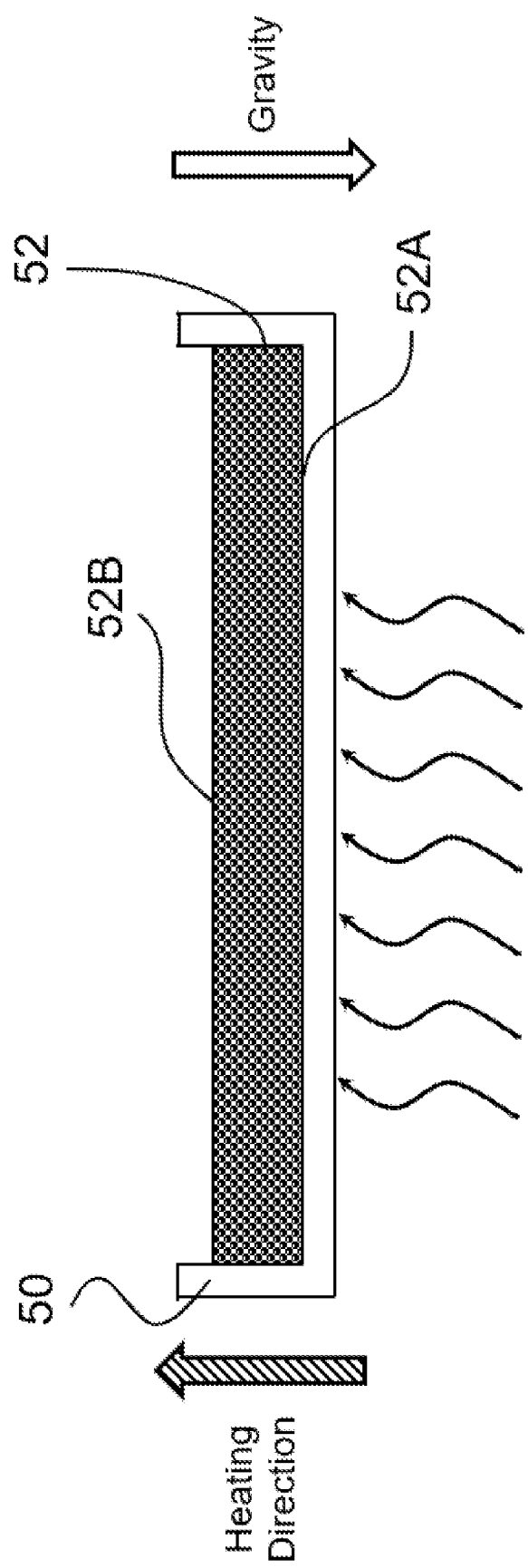
FIG. 4 shows a bottom conduction-based heating/drying arrangement for making a flexible, porous, dissolvable sheet in a batch process.

FIG. 4 shows a bottom conduction-based heating/drying arrangement for making a flexible, porous, dissolvable sheet, according to one embodiment of the present invention. Specifically, a mold 50 is filled with an aerated wet pre-mixture, which forms a sheet 52 having a first side 52A (i.e., the bottom side) and an opposing second side 52B (i.e., the top side). Such mold 50 is placed on a heated surface (not shown), for example, on top of a pre-heated Peltier plate with a controlled surface temperature of about 125-130° C., for approximately 30 minutes during the drying step. Heat is conducted from the heated surface at the bottom of the mold 50 through the mold to heat the sheet 52 from below, i.e., along an upward heating direction (as shown by the cross-hatched arrowhead), which forms a temperature gradient in the sheet 52 that decreases from the first side 52A (the bottom side) to the opposing second side 52B (the top side). Such an upward heating direction is opposite to the gravitational direction (as shown by the white arrowhead), and it is maintained as so throughout the entire drying time (i.e., the heating direction is opposite to the gravitational direction for almost 100% of the drying time). During drying, the gravitational force still drains the liquid pre-mixture downward toward the bottom region. However, the upward heating direction dries the sheet from bottom up, and water vapor generated by heat at the bottom region arises upward to escape from the solidifying matrix, so the downward liquid drainage toward the bottom region is significantly limited and "counteracted"/reduced by the solidifying matrix and the uprising water vapor. Correspondingly, the bottom region of the resulting dry sheet is less dense and contains numerous pores with relatively thin cell walls. Further, because the top region is the last region that is dried during this process, the air bubbles in the top region have sufficient time to expand to form significantly larger open pores at the top surface of the resulting sheet, which are particularly effective in facilitating water ingress into the sheet. Moreover, the resulting sheet has a more evenly distributed overall pore sizes throughout different regions (e.g., top, middle, bottom) thereof.

Figure 5:
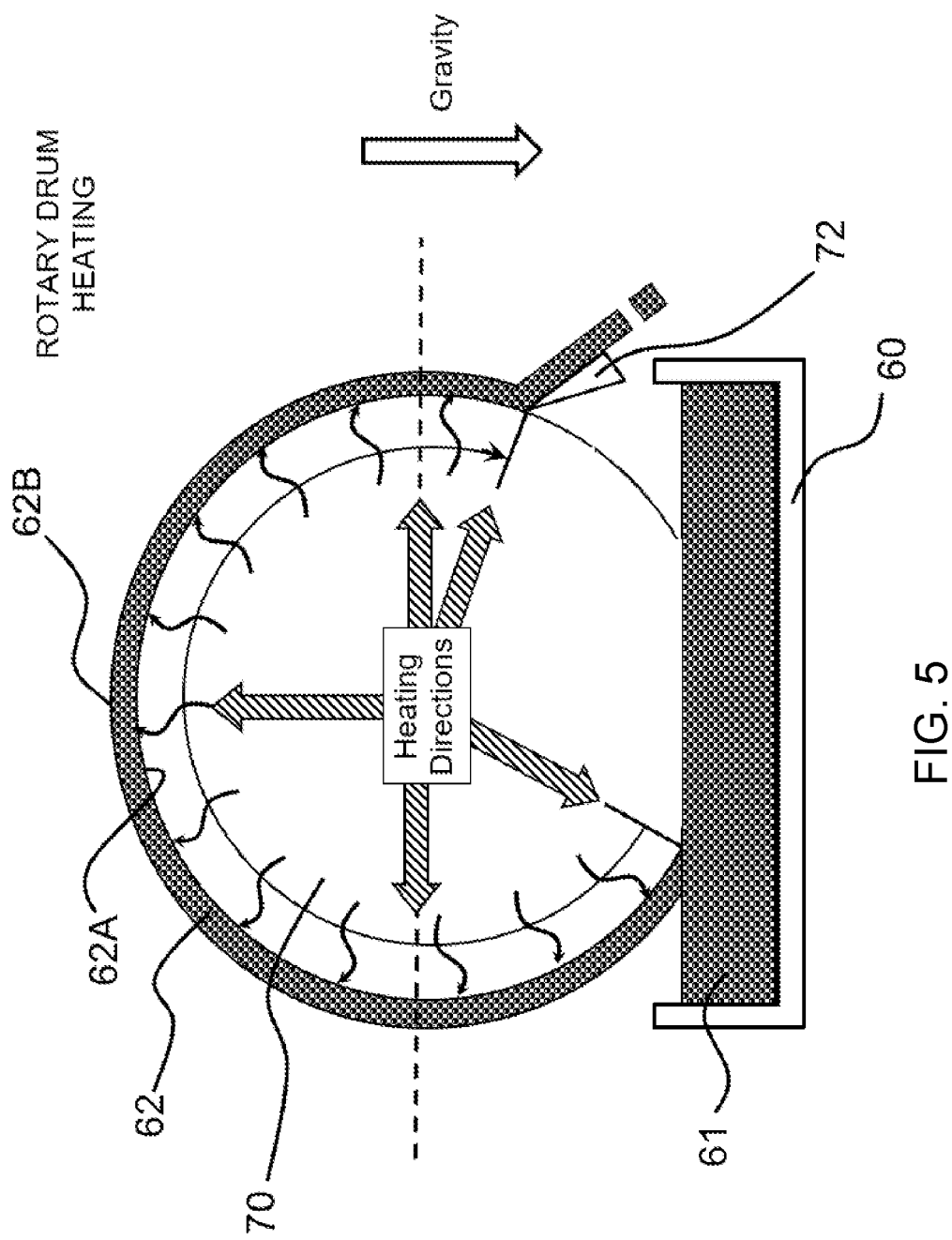
FIG. 5 shows a rotary drum-based heating/drying arrangement for making another flexible, porous, dissolvable sheet in a continuous process.

FIG. 5 shows a rotary drum-based heating/drying arrangement for making a flexible, porous, dissolvable sheet, according to another embodiment of the present invention. Specifically, a feeding trough 60 is filled with an aerated wet pre-mixture 61. A heated rotatable cylinder 70 (also referred to as a drum dryer) is placed above the feeding trough 60. The heated drum dryer 70 has a cylindrical heated outer surface characterized by a controlled surface temperature of about 130° C., and it rotates along a clock-wise direction (as shown by the thin curved line with an arrowhead) to pick up the aerated wet pre-mixture 61 from the feeding trough 60. The aerated wet pre-mixture 61 forms a thin sheet 62 over the cylindrical heated outer surface of the drum dryer 70, which rotates and dries such sheet 62 of aerated wet pre-mixture in approximately 10-15 minutes. A leveling blade (not shown) may be placed near the slurry pick-up location to ensure a consistent thickness of the sheet 62 so formed, although it is possible to control the thickness of sheet 62 simply by modulating the viscosity of the aerated wet pre-mixture 61 and the rotating speed and surface temperature of the drum dryer 70. Once dried, the sheet 62 can then picked up, either manually or by a scraper 72 at the end of the drum rotation.

As shown in FIG. 5, the sheet 62 formed by the aerated wet pre-mixture 61 comprises a first side 62A (i.e., the bottom side) that directly contacts the heated outer surface of the heated drum dryer 70 and an opposing second side 62B (i.e., the top side). Correspondingly, heat from the drum dryer 70 is conducted to the sheet 62 along an outward heating direction, to heat the first side 62A (the bottom side) of the sheet 62 first and then the opposing second side 62B (the top side). Such outward heating direction forms a temperature gradient in the sheet 62 that decreases from the first side 62A (the bottom side) to the opposing second side 62B (the top side). The outward heating direction is slowly and constantly changing as the drum dryer 70 rotates, but along a very clear and predictable path (as shown by the multiple outwardly extending cross-hatched arrowheads in FIG. 4). The relative position of the outward heating direction and the gravitational direction (as shown by the white arrowhead) is also slowing and constantly changing in a similar clear and predictable manner. For less than half of the drying time (i.e., when the heating direction is below the horizontal dashed line), the outward heating direction is substantially aligned with the gravitational direction with an offset angle of less than 90° in between. During majority of the drying time (i.e., when the heating direction is flushed with or above the horizontal dashed line), the outward heating direction is opposite or substantially opposite to the gravitational direction with an offset angle of 90° or more therebetween. Depending on the initial "start" coating position of the sheet 62, the heating direction can be opposite or substantially opposite to the gravitational direction for more than 55% of the drying time (if the coating starts at the very bottom of the drum dryer 70), preferably more than 60% of the drying time (if the coating starts at a higher position of the drum dryer 70, as shown in FIG. 5). Consequently, during most of the drying step this slowing rotating and changing heating direction in the rotary drum-based heating/drying arrangement can still function to limit and "counteract"/reduce the liquid drainage in sheet 62 caused by the gravitational force, resulting in improved OCF structures in the sheet so formed. The resulting sheet as dried by the heated drum dryer 70 is also characterized by a less dense bottom region with numerous more evenly sized pores, and a top surface with relatively larger pore openings. Moreover, the resulting sheet has a more evenly distributed overall pore sizes throughout different regions (e.g., top, middle, bottom) thereof.

IV. Physical Characteristics of Inventive Solid Sheet Articles

The flexible, porous, dissolvable solid sheet article in the present invention is characterized by improved pore structures that allows easier water ingress into the sheet article and faster dissolution of the sheet article in water.

In general, such solid sheet article may be characterized by: (i) a Percent Open Cell Content of from about 80% to 100%, preferably from about 85% to 100%, more preferably from about 90% to 100%, as measured by the Test 3 hereinafter; and (ii) an Overall Average Pore Size of from about 100 µm to about 2000 µm, preferably from about 150 µm to about 1000 µm, more preferably from about 200 µm to about 600 µm, as measured by the Micro-CT method described in Test 2 hereinafter. The Overall Average Pore Size defines the porosity of the OCF structure of the present invention. The Percent Open Cell Content defines the interconnectivity between pores in the OCF structure of the present invention. Interconnectivity of the OCF structure may also be described by a Star Volume or a Structure Model Index (SMI) as disclosed in WO2010077627 and WO2012138820.

Such solid sheet article of the present invention has opposing top and bottom surfaces, while its top surface may be characterized by a Surface Average Pore Diameter that is greater than about 300 µm, preferably greater than about 310 µm, preferably greater than about 320 µm, more preferably greater than about 330 µm, most preferably greater than about 350 µm, as measured by the SEM method described in Test 1 hereinafter.

Still further, the solid sheet article of the present invention may be characterized by an uniform pore size distribution between different regions along its thickness direction. Specifically, the solid sheet article of the present invention comprises a top region adjacent to the top surface, a bottom region adjacent to the bottom surface, and a middle region therebetween, while the top, middle, and bottom regions all have the same thickness. Each of the top, middle and bottom regions of such solid sheet article is characterized by an Average Pore Size, while the ratio of Average Pore Size in the bottom region over that in the top region (i.e., bottom-to-top Average Pore Size ratio) may be from about 0.6 to about 1.5, preferably from about 1 to about 1.2. Moreover, the solid sheet article of the present invention may be characterized by a bottom-to-middle Average Pore Size ratio of from about 0.5 to about 1.5, preferably from about 0.9 to about 1.1, and a middle-to-top Average Pore Size ratio of from about 1 to about 1.5, preferably from about 1 to about 1.2.

Preferably, the solid sheet article of the present invention is further characterized by an Average Cell Wall Thickness of from about 5 µm to about 200 µm, preferably from about 10 µm to about 100 µm, more preferably from about 10 µm to about 80 µm, as measured by Test 2 hereinafter.

The solid sheet article of the present invention may contain a small amount of water. Preferably, it is characterized by a final moisture content of from about 0.5% to about 25%, preferably from about 1% to about 20%, more preferably from about 3% to about 15%, by weight of the solid sheet article, as measured by Test 4 hereinafter.

Each sheet of the solid sheet article of the present invention may have a thickness ranging from about 0.6 mm to about 3.5 mm, preferably from about 0.7 mm to about 3 mm, more preferably from about 0.8 mm to about 2 mm, most preferably from about 1 mm to about 1.5 mm. Thickness of the solid sheet article can be measured using Test 6 described hereinafter.

The solid sheet article of the present invention may further be characterized by a basis weight of from about 50 grams/m² to about 250 grams/m², preferably from about 80 grams/m² to about 230 grams/m², more preferably from about 100 grams/m² to about 220 grams/m², as measured by Test 6 described hereinafter.

Still further, the solid sheet article of the pre sent invention may have a density ranging from about 0.05 grams/cm³ to about 0.5 grams/cm³, preferably from about 0.06 grams/cm³ to about 0.4 grams/cm³, more preferably from about 0.07 grams/cm³ to about 0.3 grams/cm³, most preferably from about 0.08 grams/cm³ to about 0.25 grams/cm³, as measured by Test 7 hereinafter. Density of the solid sheet article of the present invention may be lower than that of the sheet of aerated wet pre-mixture, also due to pore expansion that in turn leads to overall volume expansion.

Furthermore, the solid sheet article of the present invention can be characterized by a Specific Surface Area of from about 0.03 m²/g to about 0.25 m²/g, preferably from about 0.04 m²/g to about 0.22 m²/g, more preferably from 0.05 m²/g to 0.2 m²/g, most preferably from 0.1 m²/g to 0.18 m²/g, as measured by Test 8 described hereinafter. The Specific Surface Area of the solid sheet article of the present invention may be indicative of its porosity and may impact its dissolution rate, e.g., the greater the Specific Surface Area, the more porous the sheet article and the faster its dissolution rate.

V. Conversion of Multiple Sheets into Multilayer Structures

Once the flexible, dissolvable, porous solid sheet of the present invention is formed, as described hereinabove, two or more of such sheets can be further combined and/or treated to form dissolvable solid sheet articles of any desirable three-dimensional shapes, including but not limited to: spherical, cubic, rectangular, oblong, cylindrical, rod, sheet, flower-shaped, fan-shaped, star-shaped, disc-shaped, and the like. The sheets can be combined and/or treated by any means known in the art, examples of which include but are not limited to, chemical means, mechanical means, and combinations thereof. Such combination and/or treatment steps are hereby collectively referred to as a "conversion" process, i.e., which functions to convert two or more flexible, dissolvable, porous sheets of the present invention into a dissolvable solid sheet article with a desired three-dimensional shape.

Conventional dissolvable solid articles have relatively high length/width-to-thickness ratios, i.e., they are relatively thin, in order to ensure fast dissolution of such articles in water. Therefore, such dissolvable solid articles typically are typically provided in form of relatively large but thin sheet products, which may be difficult to handle (e.g., too floppy and easily sticking together and hard to separate upon use) and are not aesthetically pleasing to the consumers. However, there is little or no space for change or improvement of such product form, due to constraints imparted by the dissolution requirement.

It has been a surprising and unexpected discovery of the present invention that three-dimensional multilayer solid articles formed by stacking multiple layers of the solid sheets of the present invention together are more dissolvable than single-layer solid articles that have the same aspect ratio. This allows significant extension of such solid articles along the thickness direction, to create three-dimensional product shapes that are easier to handle and more aesthetically pleasing to the consumers (e.g., products in form of thick pads or even cubes).

Specifically, the multilayer dissolvable solid articles formed by stacking multiple layers of the solid sheets of the present invention together is characterized by a maximum dimension D and a minimum dimension z (which is perpendicular to the maximum dimension), while the ratio of D/z (hereinafter also referred to as the "Aspect Ratio") ranges from 1 to about 10, preferably from about 1.4 to about 9, preferably from about 1.5 to about 8, more preferably from about 2 to about 7. Note that when the Aspect Ratio is 1, the dissolvable solid article has a spherical shape. When the Aspect Ratio is about 1.4, the dissolvable solid article has a cubical shape.

The multilayer dissolvable solid article of the present invention may have a minimal dimension z that is greater than about 3 mm but less than about 20 cm, preferably from about 4 mm to about 10 cm, more preferably from about 5 mm to about 30 mm.

The above-described multilayer dissolvable solid article may comprise two or more such flexible, dissolvable, porous sheets. For example, it may comprise from about 2 to about 50, preferably from about 3 to about 40, more preferably from about 4 to about 30, of the flexible, dissolvable, porous sheets. The improved OCF structures in the flexible, dissolvable, porous sheets made according to the present invention allow stacking of many sheets (e.g., 15-40) together, while still providing a satisfactory overall dissolution rate for the stack.

Further, the solid sheet article of the present invention may comprise two or more flexible, porous, dissolvable sheets, wherein a coating composition is present on at least one surface of at least one of the two or more sheets, provided that the coating composition is not on any of the outer surfaces of the solid sheet article. In other words, one or more functional ingredients can be "sandwiched" between individual sheets of the multilayer dissolvable solid article as described hereinabove. Particularly, the coating composition may be applied between individual sheets of the multilayer dissolvable solid article by any appropriate means, e.g., by spraying, sprinkling dusting, coating, spreading, dipping, injecting, rolling, or even vapor deposition. More particularly, the coating composition may be applied on one or both of contacting surfaces of adjacent sheets in the stack.

Preferably, as mentioned hereinabove, the coating composition may comprise a silicone and/or other ingredients including an additional surfactant (for example, a non-ionic surfactant), perfume and a rheology modifier. The coating composition may have a viscosity of from about 1 cps to about 25,000 cps, preferably from about 2 cps to about 10,000 cps, more preferably from about 3 cps to about 5,000 cps, most preferably from about 1,000 cps to about 5,000 cps, as measured at about 20° C. and 1 s$^{-1}$. The viscosity values are measured using a Malvern Kinexus Lab+ rheometer with cone and plate geometry (CP1/50 SR3468 SS), a gap width of 0.054 mm, a temperature of 20° C. and a shear rate of 1.0 reciprocal seconds for a period of 360 seconds. It has been a surprising and unexpected discovery of the present invention that three-dimensional multilayer solid articles containing the coating composition have significantly improved dissolution profiles than multilayer solid articles having the same amount of active ingredients but without the coating composition. Further, the solid sheet articles comprising the coating composition may provide additional benefits including improved softness performance and/or anti-wrinkle effect compared to the solid sheet articles without the coating composition.

Further, in order to avoid interference of such functional ingredients with the cutting seal or edge seal near the peripherals of the individual sheets, it is preferred that such functional ingredients are located within a central region between two adjacent sheets, which is defined as a region that is spaced apart from the peripherals of such adjacent sheets by a distance that is at least 10% of the maximum Dimension D. Preferably, the weight ratio of the coating composition to the sheets in the solid sheet article is from about 0.01 to about 2, preferably from about 0.02 to about 1, more preferably from about 0.05 to about 0.8, and most preferably from about 0.08 to about 0.5 for example, about 0.01, about 0.02, about 0.03, about 0.04, about 0.05, about 0.06, about 0.07, about 0.08, about 0.09, about 0.1, about 0.15, about 0.2, about 0.3, about 0.4, about 0.5 or any ranges therebetween.

TEST METHODS

Test 1: Scanning Electron Microscopic (SEM) Method for Determining Surface Average Pore Diameter of the Sheet Article A Hitachi TM3000 Tabletop Microscope (S/N: 123104-04) is used to acquire SEM micrographs of samples. Samples of the solid sheet articles of the present invention are approximately 1 cm×1 cm in area and cut from larger sheets. Images are collected at a magnification of 50×, and the unit is operated at 15 kV. A minimum of 5 micrograph images are collected from randomly chosen locations across each sample, resulting in a total analyzed area of approximately 43.0 mm$^2$ across which the average pore diameter is estimated.

The SEM micrographs are then firstly processed using the image analysis toolbox in Matlab. Where required, the images are converted to gray scale. For a given image, a histogram of the intensity values of every single pixel is generated using the 'imhist' Matlab function. Typically, from such a histogram, two separate distributions are obvious, corresponding to pixels of the brighter sheet surface and pixels of the darker regions within the pores. A threshold value is chosen, corresponding to an intensity value between the peak value of these two distributions. All pixels having an intensity value lower than this threshold value are then set to an intensity value of 0, while pixels having an intensity value higher are set to 1, thus producing a binary black and white image. The binary image is then analyzed using ImageJ (https://imagej.nih.gov, version 1.52a), to examine both the pore area fraction and pore size distribution. The scale bar of each image is used to provide a pixel/mm scaling factor. For the analysis, the automatic thresholding and the analyze particles functions are used to isolate each pore. Output from the analyze function includes the area fraction for the overall image and the pore area and pore perimeter for each individual pore detected.

Average Pore Diameter is defined as $D_A50$:50% of the total pore area is comprised of pores having equal or smaller hydraulic diameters than the $D_A50$ average diameter.

Hydraulic diameter='4*Pore area $(m^2)$/Pore perimeter $(m)$'.

It is an equivalent diameter calculated to account for the pores not all being circular.

Test 2: Micro-Computed Tomographic (µCT) Method for Determining Overall or Regional Average Pore Size and Average Cell Wall Thickness of the Open Cell Foams (OCF)

Porosity is the ratio between void-space to the total space occupied by the OCF. Porosity can be calculated from µCT scans by segmenting the void space via thresholding and determining the ratio of void voxels to total voxels. Similarly, solid volume fraction (SVF) is the ratio between solid-space to the total space, and SVF can be calculated as the ratio of occupied voxels to total voxels. Both Porosity and SVF are average scalar-values that do not provide structural information, such as, pore size distribution in the height-direction of the OCF, or the average cell wall thickness of OCF struts.

To characterize the 3D structure of the OCFs, samples are imaged using a µCT X-ray scanning instrument capable of acquiring a dataset at high isotropic spatial resolution. One example of suitable instrumentation is the SCANCO system model 50 µCT scanner (Scanco Medical AG, Bruttisellen, Switzerland) operated with the following settings: energy level of 45 kVp at 133 µA; 3000 projections; 15 mm field of view; 750 ms integration time; an averaging of 5; and a voxel size of 3 µm per pixel. After scanning and subsequent data reconstruction is complete, the scanner system creates a 16 bit data set, referred to as an ISQ file, where grey levels reflect changes in x-ray attenuation, which in turn relates to material density. The ISQ file is then converted to 8 bit using a scaling factor.

Scanned OCF samples are normally prepared by punching a core of approximately 14 mm in diameter. The OCF punch is laid flat on a low-attenuating foam and then mounted in a 15 mm diameter plastic cylindrical tube for scanning. Scans of the samples are acquired such that the entire volume of all the mounted cut sample is included in the dataset. From this larger dataset, a smaller sub-volume of the sample dataset is extracted from the total cross section of the scanned OCF, creating a 3D slab of data, where pores can be qualitatively assessed without edge/boundary effects.

To characterize pore-size distribution in the height-direction, and the strut-size, Local Thickness Map algorithm, or LTM, is implemented on the subvolume dataset. The LTM Method starts with a Euclidean Distance Mapping (EDM) which assigns grey level values equal to the distance each void voxel is from its nearest boundary. Based on the EDM data, the 3D void space representing pores (or the 3D solid space representing struts) is tessellated with spheres sized to match the EDM values. Voxels enclosed by the spheres are assigned the radius value of the largest sphere. In other words, each void voxel (or solid voxel for struts) is assigned the radial value of the largest sphere that that both fits within the void space boundary (or solid space boundary for struts) and includes the assigned voxel.

The 3D labelled sphere distribution output from the LTM data scan can be treated as a stack of two dimensional images in the height-direction (or Z-direction) and used to estimate the change in sphere diameter from slice to slice as a function of OCF depth. The strut thickness is treated as a 3D dataset and an average value can be assessed for the whole or parts of the subvolume. The calculations and measurements were done using AVIZO Lite (9.2.0) from ThermoFisher Scientific and MATLAB (R2017a) from Mathworks.

Test 3: Percent Open Cell Content of the Sheet Article

The Percent Open Cell Content is measured via gas pycnometry. Gas pycnometry is a common analytical technique that uses a gas displacement method to measure volume accurately. Inert gases, such as helium or nitrogen, are used as the displacement medium. A sample of the solid sheet article of the present invention is sealed in the instrument compartment of known volume, the appropriate inert gas is admitted, and then expanded into another precision internal volume. The pressure before and after expansion is measured and used to compute the sample article volume.

ASTM Standard Test Method D2856 provides a procedure for determining the percentage of open cells using an older model of an air comparison pycnometer. This device is no longer manufactured. However, one can determine the percentage of open cells conveniently and with precision by performing a test which uses Micromeritics' AccuPyc Pycnometer. The ASTM procedure D2856 describes 5 methods (A, B, C, D, and E) for determining the percent of open cells of foam materials. For these experiments, the samples can be analyzed using an Accupyc 1340 using nitrogen gas with the ASTM foampyc software. Method C of the ASTM procedure is to be used to calculate to percent open cells. This method simply compares the geometric volume as determined using calipers and standard volume calculations to the open cell volume as measured by the Accupyc, according to the following equation:

Open cell percentage=Open cell volume of sample/ Geometric volume of sample*100

It is recommended that these measurements be conducted by Micromeretics Analytical Services, Inc. (One Micromeritics Dr, Suite 200, Norcross, Ga. 30093). More information on this technique is available on the Micromeretics Analytical Services web sites (www.particletesting.com or www.micromeritics.com), or published in "Analytical Methods in Fine particle Technology" by Clyde Orr and Paul Webb.

Test 4: Final Moisture Content of the Sheet Article

Final moisture content of the solid sheet article of the present invention is obtained by using a Mettler Toledo HX204 Moisture Analyzer (S/N B706673091). A minimum of 1 g of the dried sheet article is placed on the measuring tray. The standard program is then executed, with additional program settings of 10 minutes analysis time and a temperature of 110° C.

Test 5: Thickness of the Sheet Article

Thickness of the flexible, porous, dissolvable solid sheet article of the present invention is obtained by using a micrometer or thickness gage, such as the Mitutoyo Corporation Digital Disk Stand Micrometer Model Number IDS-1012E (Mitutoyo Corporation, 965 Corporate Blvd, Aurora, Ill., USA 60504). The micrometer has a 1-inch diameter platen weighing about 32 grams, which measures thickness at an application pressure of about 0.09 psi (6.32 gm/cm$^2$).

The thickness of the flexible, porous, dissolvable solid sheet article is measured by raising the platen, placing a section of the sheet article on the stand beneath the platen, carefully lowering the platen to contact the sheet article, releasing the platen, and measuring the thickness of the sheet article in millimeters on the digital readout. The sheet article should be fully extended to all edges of the platen to make sure thickness is measured at the lowest possible surface pressure, except for the case of more rigid substrates which are not flat.

Test 6: Basis Weight of the Sheet Article

Basis Weight of the flexible, porous, dissolvable solid sheet article of the present invention is calculated as the weight of the sheet article per area thereof (grams/m$^2$). The area is calculated as the projected area onto a flat surface perpendicular to the outer edges of the sheet article. The solid sheet articles of the present invention are cut into sample squares of 10 cm×10 cm, so the area is known. Each of such sample squares is then weighed, and the resulting weight is then divided by the known area of 100 cm$^2$ to determine the corresponding basis weight.

For an article of an irregular shape, if it is a flat object, the area is thus computed based on the area enclosed within the outer perimeter of such object. For a spherical object, the area is thus computed based on the average diameter as 3.14×(diameter/2)$^2$. For a cylindrical object, the area is thus computed based on the average diameter and average length as diameter×length. For an irregularly shaped three-dimensional object, the area is computed based on the side with the largest outer dimensions projected onto a flat surface oriented perpendicularly to this side. This can be accomplished by carefully tracing the outer dimensions of the object onto a piece of graph paper with a pencil and then computing the area by approximate counting of the squares and multiplying by the known area of the squares or by taking a picture of the traced area (shaded-in for contrast) including a scale and using image analysis techniques.

Test 7: Density of the Wet Pre-Mixture and Sheet Article

Density of the wet pre-mixture is determined by the equation: Calculated Density=Weight of the wet pre-mixture per one liter (g/ml).

Density of the flexible, porous, dissolvable solid sheet article of the present invention is determined by the equation: Calculated Density=Basis Weight of porous solid/ (Porous Solid Thickness×1,000). The Basis Weight and Thickness of the dissolvable porous solid are determined in accordance with the methodologies described hereinabove.

Test 8: Specific Surface Area of the Sheet Article

The Specific Surface Area of the flexible, porous, dissolvable solid sheet article is measured via a gas adsorption technique. Surface Area is a measure of the exposed surface of a solid sample on the molecular scale. The BET (Brunauer, Emmet, and Teller) theory is the most popular model used to determine the surface area and is based upon gas adsorption isotherms. Gas Adsorption uses physical adsorption and capillary condensation to measure a gas adsorption isotherm. The technique is summarized by the following steps; a sample is placed in a sample tube and is heated under vacuum or flowing gas to remove contamination on the surface of the sample. The sample weight is obtained by subtracting the empty sample tube weight from the combined weight of the degassed sample and the sample tube. The sample tube is then placed on the analysis port and the analysis is started. The first step in the analysis process is to evacuate the sample tube, followed by a measurement of the free space volume in the sample tube using helium gas at liquid nitrogen temperatures. The sample is then evacuated a second time to remove the helium gas. The instrument then begins collecting the adsorption isotherm by dosing krypton gas at user specified intervals until the requested pressure measurements are achieved. Samples may then analyzed using an ASAP 2420 with krypton gas adsorption. It is recommended that these measurements be conducted by Micromeretics Analytical Services, Inc. (One Micromeritics Dr, Suite 200, Norcross, Ga. 30093). More information on this technique is available on the Micromeretics Analytical Services web sites (www.particletesting.com or www.micromeritics.com), or published in a book, "Analytical Methods in Fine Particle Technology", by Clyde Orr and Paul Webb.

Test 9: Dissolution Rate

Firstly, the solid sheets are stored under ambient relative humidity of 50±2% and ambient temperature of 23±1° C. for 24 hours (i.e., a conditioning step). Following the initial conditioning step described above, 25 mm diameter discs are firstly cut from the large solid sheet using a 25 mm hollow hole punch. The required number of foam discs is set such that the total mass of all foam discs is no less than 0.1 g.

The required number of foam discs are then stacked in a head to toe orientation and placed inside an Omnifit™ EZ chromatography column (006EZ-25-10-AF) having 25 mm inner diameter, 100 m length and an adjustable, removable endpiece. The stack of foam discs is placed inside the column such that the direction of flow through the column is perpendicular to the top surface of the foam discs. Once placed inside the column, the endpiece is inserted into the column and adjusted until the perpendicular distance between the two inner frits is equal to the thickness of the stack of foam discs.

Masterflex silicone tubing (MFLEX SILICONE #25 25') and a Masterflex peristaltic pump (MFLX L/S 1CH 300R 115/230 13124) are used to control the flow of water through the column. The system flow rate is calibrated by flowing water through the pump, tubing and an empty column at different pump RPM settings and recording the volume of water collected over a defined period of time. For all experiments a flow rate of 5 litres per hour was utilized.

The inlet and outlet tubing are both placed inside a 1 litre beaker containing 500 ml of deionised water at ambient temperature. The beaker is placed on a magnetic stirrer plate, and a magnetic stirrer bar having length 23 mm and thickness 10 mm is placed in the beaker, and the stirrer rotation speed is set to 300 rpm. A Mettler Toledo 5230 conductivity meter is calibrated to 1413 µS/cm and the probe placed in the beaker of water.

The flow of water through the system is started. Once the first drops of water can be visibly seen inside the column and in contact with the foam, the data recording function of the conductivity meter is started. Data is recorded for at least 20 minutes.

In order to estimate the time required to reach a 90 or 95% percentage dissolution of the foam, a calibration curve is firstly generated where layers of the foam discs are dropped one a time into a stirred beaker of 500 ml deionised water. The mass of each individual foam disc, and the conductivity after 5 minutes are both recorded. This process is repeated for up to 5 discs total. A linear function is fitted to the data, which is then used to estimate the maximum conductivity in each dissolution experiment based on the total mass of the foam discs placed in the column. The percentage dissolution is then calculated as % Dissolution=Experimentally measured conductivity/Maximum conductivity*100

The time required to achieve 90 or 95 percentage dissolution is then found from this calculated data. The calibration procedure is repeated for each formula tested.

Test 10: Elasticity of Solid Sheets

The extension of solid sheets is determined as the measurement for elasticity of solid sheets by employing a Material Testing System instrument (MTS Tensile Tester Criterion® Series, Model 42). The solid sheets are pre-conditioned and equilibrated for 24 hours at a relative humidity of 10% and at 23+/−1° C. After pre-conditioning, a test sample (e.g. a strip) is cut with a width of 20 mm and a length of 100 mm. The test strips are clamped firmly on both sides to the mount of the instrument (to such an extent as to prevent slipping during the test) and a load is applied at a constant head speed of 200 mm per minute to stretch the strip at the mid-point at a rate of 100 mm per minute. The Strain at Break (mm) is recorded as the total distance of elongation of the strip (i.e., the extension) when it breaks.

Test 11: Softness Performance of Solid Sheets

The softness performance of solid sheets is measured as follows:

Multiple semi-automatic washing machines (e.g. Haier XPB60-187BS FM) are used. This semi-automatic washing machine contains two parts: a tub for washing and rinsing and a spinner for spin-dry. Each machine is operated according to the following steps: (1) a recommended amount of washing powder (further described below) is dissolved in an appropriate amount of water (e.g. 32 g of powder in 13 L of water for 2 minutes); (2) the fabrics are manually added into the water in the tub; (3) the fabrics are allowed to soak for a while (e.g. 3 minutes) without agitation; (4) a standard automatic machine washing (e.g. 20 minutes); (5) 2 consecutive rinses (e.g. 1 minute spin dry in the spinner and 3 minutes washing agitation with 23 L water in the tub); and (6) final rinsing during which the test sample is added. In Step (6), particularly, after the addition of 13 L of water into the tub, the test sample is then added into this water and then the automated machine agitation runs for 2 minutes to ensure full dissolution of the sample. The previously spin-dried fabric is then added back into the solution in the tub and the automated machine agitation runs for 1 minute. The fabric is then spin-dried for 30 seconds and left sitting in the spinner for 10 minutes before removal.

The water used has a hardness of 74 ppm hardness, which contains 61 ppm $CaCl_2$ and 13 ppm $MgCl_2$ and a temperature of 28° C. in all soak, wash, rinse steps. The total fabric load weight is 1.2 kg (which includes 4 test fabric hand towel terry cloths, and the remaining items consisting of cotton fabric only and poly-cotton mixture with a 6:4 ratio). The detergent used is ARIEL powder detergent from Philippine (produced by The Procter & Gamble Company). 32 g of detergent is dosed into the wash water. The test fabric terry cloths are line dried for 36-48 hours in a 32° C./80% relative humidity controlled room.

To quantify softness, the coefficient of friction of each terry cloth is measured. The kinematic coefficient of friction is measured using a Thwing Albert Friction/Peel Tester FP-2250 by attaching a swatch cut from the terry cloth to a sled and dragging the sled over a portion of the remaining terry cloth at a fixed rate. A lower measured coefficient of friction indicates improved softness performance.

Test 12: Anti-Wrinkle Effect of Solid Sheets

The anti-wrinkle effect of solid sheets is measured as follows:

Multiple semi-automatic washing machines (e.g. Haier XPB60-187BS FM) are used. This semi-automatic washing machine contains two parts: a tub for washing and rinsing and a spinner for spin-dry. Each machine is operated according to the following steps: (1) a recommended amount of washing powder (further described below) is dissolved in an appropriate amount of water (e.g. 32 g of powder in 13 L of water for 2 minutes); (2) the fabrics are manually added into the water in the tub; (3) the fabrics are allowed to soak for a while (e.g. 3 minutes) without agitation; (4) a standard automatic machine washing (e.g. 20 minutes); (5) 2 consecutive rinses (e.g. 1 minute spin dry in the spinner and 3 minutes washing agitation with 23 L water in the tub); and (6) final rinsing during which the test sample is added. In Step (6), particularly, after the addition of 13 L of water into the tub, the test sample is then added into this water and then the automated machine agitation runs for 2 minutes to ensure full dissolution of the sample. The previously spin-dried fabric is then added back into the solution in the tub and the automated machine agitation runs for 1 minute. The fabric is then spin-dried for 30 seconds and left sitting in the spinner for 10 minutes before removal.

The water used has a hardness of 74 ppm hardness, which contains 61 ppm $CaCl_2$ and 13 ppm $MgCl_2$ and a temperature of 28° C. in all soak, wash, rinse steps. The total fabric load weight is 1.2 kg (which includes 4 test polyester fabric, 4 test polycotton fabric 4 test knitted cotton fabric and 4 test woven cotton fabric, and the remaining items consisting of cotton fabric only and poly-cotton mixture with a 6:4 ratio). The detergent used is ARIEL powder detergent from Philippine (produced by The Procter & Gamble Company). 32 g of detergent is dosed into the wash water. The test fabric terry cloths are line dried for 36-48 hours in a 32° C./80% relative humidity controlled room.

To evaluate wrinkling, washed and line dried fabrics are visually assessed by a panel of trained operators. In each panel test, the panelists are presented with 16 polyester fabrics total, consisting of 4 sets of 4 fabrics, where each set corresponds to a softness product that the fabrics in that set have been washed with, or always in the case of 1 set a control where 40 ml Downy Fabric Conditioner from Philippine (produced by The Procter & Gamble Company) is used. The washed and line dried test fabrics are ranked by each individual panelist independently, with each panelist assigning the most visually wrinkled fabric set a grade score of 4 and the least winkled fabric set a grade score of 1. Each panel contains 6 to 8 individuals. The grade scores assigned for each softness product are averaged and a standard deviation is calculated to determine the variability between panelists. Exact same evaluation method is also applied to other types of test fabrics.

EXAMPLES

Example 1: Improved Stability of Aerated Pre-Mixture with a Preferred Range of Ratio of the Plasticizer to the Cationic Surfactant Solid sheets with the formulations (Formulation A and Comparative Formulations a and b) as shown in the following Table 1 (wet pre-mixture) and Table 2 (dry sheet) are prepared according to the rotary drum-based heating/drying arrangement in the Section III: PROCESSES FOR MAKING SOLID SHEETS.

TABLE 1

| | Wet pre-mixture | | |
|---|---|---|---|
| Materials (wt %) | Formulation A | Comparative Formulation a | Comparative Formulation b |
| $PVA^a$ | 9.8 | 15.6 | 2.5 |
| Glycerin | 13.7 | 8.0 | 21.1 |
| $DEEDMAC^b$ | 10.1 | 10.1 | 10.1 |
| Starch | 1.3 | 1.3 | 1.3 |
| Water Content | Balance | Balance | Balance |
| Ratio of Glycerin to DEEDMAC | 1.36 | 0.79 | 2.09 |

$^a$Polyvinyl alcohol having a hydrolysis level of 88% and a degree of polymerization of about 1700, available from Sigma Aldrich.
$^b$Rewoquat DEEDMAC available from Evonik Industries.

TABLE 2

| | Dry sheet | | |
|---|---|---|---|
| Materials (wt %) | Formulation A | Comparative Formulation a | Comparative Formulation b |
| $PVA^a$ | 25.3 | 40.2 | 6.4 |
| Glycerin | 35.4 | 20.5 | 54.2 |
| $DEEDMAC^b$ | 25.9 | 25.9 | 25.9 |
| Starch | 3.4 | 3.4 | 3.4 |
| Water Content | Balance | Balance | Balance |
| Ratio of Glycerin to DEEDMAC | 1.36 | 0.79 | 2.09 |

$^a$Polyvinyl alcohol having a hydrolysis level of 88% and a degree of polymerization of about 1700, available from Sigma Aldrich.
$^b$Rewoquat DEEDMAC available from Evonik Industries.

Specifically, a wet pre-mixture (i.e., a slurry) containing the ingredients of solid sheets and additional water is first prepared, to result in a total solids content of about 35% by weight (i.e., the total water content in the slurry is about 65% by weight). The method of slurry preparation is as follows:

1. Water and glycerin are firstly added together into a glass beaker and stirred at 200 rpm using an overhead stirrer.
2. While continuing to stir, the polyvinyl alcohol is then slowly added into the beaker containing water and glycerin, ensuring that no foaming of the solution or clumping of the polyvinyl alcohol occurred.
3. The beaker is then placed in a water bath and heated to 80° C. while continuing stirring. The beaker is covered with cling film or tinfoil in order to mitigate water evaporation and left to continue mixing for at least 1.0 hour.
4. The remaining components are weighed and added together in a separate glass beaker. The balance of water required to achieve 65% total water content in the slurry is also added to this beaker.
5. This beaker is placed in a water bath at 80° C., and its contents are stirred using an overhead stirrer at 500 rpm for at least 30 minutes.
6. Once the predefined mixing time is reached in both beakers, the contents of both are added together into a single glass beaker, followed by continued stirring at 500 rpm and the temperature is maintained at 80° C. for at least another 30 minutes.

Then, the pre-mixture is aerated by using Aeros A20 continuous aerator. After the aeration, the aerated pre-mixture is collected and then dried in a rotary drum drier to make solid sheets. The settings and conditions in the aeration and drum drying are shown in Table 3 below:

TABLE 3

| Parameters | Value |
| --- | --- |
| Wet pre-mixture temperature before and during aeration | 80° C. |
| Aeros feed pump speed setting | 600 |
| Aeros mixing head speed setting | 500 |
| Aeros air flow rate setting | 100 |
| Wet pre-mixture temperature before drying | 60° C. |
| Rotary drum drier surface temperature | 110° C. |
| Rotary drum drier rotational speed | 0.160 rpm |
| Drying time | 4.52 min |

Additionally, in order to compare aeration stability of pre-mixtures for different formulations, 60 ml of aerated pre-mixture is stored in a beaker, the beaker is kept in a water bath and with the water temperature sets to 60 deg C., a laboratory overhead mixer is used to continuously stir the wet pre-mixture for 30 mins at 50 RPM. The initial density of the aerated pre-mixture and the density at 30 min are measured according to Test 7: Density of the Wet Pre-mixture and Sheet Article and shown in Table 4 below. The ratio of density at 0 min to density at 30 min is used as a measurement of the stability of the aerated pre-mixture. Further, the density of solid sheets obtained by different formulations is also determined. The data in Table 4 indicates that, in comparison with the very high ratio (i.e., 2.00 or 3.07, respectively) of the density of pre-mixture at 30 min to the density of pre-mixture at 0 min for Comparative Formulation a orb in which the ratio of glycerin to DEED-MAC is too high or too low, the ratio for Formulation A is only 1.27. Particularly, in comparison with the rapidly increased density of pre-mixture (up to more than 0.800 g/ml) after the aeration for Comparative Formulations a and b, the increase in density during the 30 min storage for Formulation A is very limited (e.g. from 0.310 g/ml to 0.395 g/ml) and the density remains low (e.g. 0.395 g/ml). Further, as also shown in Table 4, the solid sheet for Formulation A has a significantly lower density compared Comparative Formulation a (0.204 g/ml vs 0.455 g/ml), and for Comparative Formulation b, no sheet is obtained because the pre-mixture is too instable. Accordingly, when the ratio of the plasticizer (e.g. glycerin) to the cationic surfactant (e.g. DEEDMAC) is within a preferred range (e.g. from 0.9 to 2), the stability of aerated pre-mixture is significantly improved.

TABLE 4

| | Formulation A | Comparative Formulation a | Comparative Formulation b |
| --- | --- | --- | --- |
| Ratio of Glycerin to DEEDMAC | 1.36 | 0.79 | 2.09 |
| Pre-mixture Density at 0 min, g/ml | 0.310 | 0.404 | 0.261 |
| Pre-mixture Density at 30 min, g/ml | 0.395 | 0.810 | 0.800 |
| Ratio of Density at 30 min to Density at 0 min | 1.27 | 2.00 | 3.07 |
| Sheet Density, g/ml | 0.204 | 0.455 | No sheet |

Example 2: Impact of Starch Level on the Elasticity of the Solid Sheets

Solid sheets with the formulations (Formulations A to C) as shown in the following Table 5 (wet pre-mixture) and Table 6 (dry sheet) are prepared according to the rotary drum-based heating/drying arrangement in the Section III: PROCESSES FOR MAKING SOLID SHEETS, similarly as Example 1.

TABLE 5

| | Wet pre-mixture | | |
| --- | --- | --- | --- |
| Materials (wt %) | Formulation B | Formulation A | Formulation C |
| PVA[a] | 11.2 | 9.8 | 9.2 |
| Glycerin | 13.7 | 13.7 | 13.7 |
| DEEDMAC[b] | 10.1 | 10.1 | 10.1 |
| Starch | 0.0 | 1.3 | 1.9 |
| Water Content | Balance | Balance | Balance |

[a]Polyvinyl alcohol having a hydrolysis level of 88% and a degree of polymerization of about 1700, available from Sigma Aldrich.
[b]Rewoquat DEEDMAC available from Evonik Industries.

TABLE 6

| | Dry sheet | | |
| --- | --- | --- | --- |
| Materials (wt %) | Formulation B | Formulation A | Formulation C |
| PVA[a] | 28.7 | 25.3 | 23.7 |
| Glycerin | 35.4 | 35.4 | 35.4 |
| DEEDMAC[b] | 25.9 | 25.9 | 25.9 |
| Starch | 0.0 | 3.4 | 5.0 |
| Water Content | Balance | Balance | Balance |

[a]Polyvinyl alcohol having a hydrolysis level of 88% and a degree of polymerization of about 1700, available from Sigma Aldrich.
[b]Rewoquat DEEDMAC available from Evonik Industries.

The extensions of solid sheets having Formulations A to C are determined according to TEST 10: Elasticity of solid sheets to characterize the elasticity of solid sheets and shown in Table 7 below. The data indicates that, in comparison with a great reduction of extension for the solid sheet with Formulation C comprising 5% of starch (i.e. 35%) the extension of the solid sheet comprising 3.4% of starch (Formulation A) is reduced by a much less degree (i.e. 21%). Accordingly, too much starch may compromise the elasticity of the sheet article. Therefore, it is further preferred that the solid sheet article comprises no more than 5% of starch by weight of the solid sheet article.

TABLE 7

| | Formulation B | Formulation A | Formulation C |
| --- | --- | --- | --- |
| Starch wt % | 0% | 3.4% | 5% |
| Extension, mm | 98.5 | 77.5 | 63.7 |
| Reduction of extension compared to Formulation B, % | — | 21% | 35% |
| Foam Density, g/ml | 0.124 | 0.14 | 0.111 |
| Thickness, mm | 1.38 | 1.64 | 1.47 |

Example 3: OCF Structures in Solid Sheets Made by Various Heating/Drying Arrangements Solid sheets with the formulations (Formulations 1 and 2) as shown in the following Table 8 (wet pre-mixture) and Table 9 (dry sheet) are prepared according to various heating/drying arrangement in the Section III: PROCESSES FOR MAKING SOLID SHEETS.

TABLE 8

Wet pre-mixture

| Materials | Formulation 1 | Formulation 2 |
|---|---|---|
| Polyvinyl alcohol (with a degree of polymerization of about 1700, a hydrolysis level of 88%) | 7.58 | 6.85 |
| Glycerin | 1.08 | 2.75 |
| Linear Alkylbenzene Sulfonate | 19.12 | — |
| Sodium Laureth-3 Sulfate | 3.61 | 3.01 |
| C12-C14 Ethoxylated alcohol | 3.61 | — |
| Sodium Lauryl Sulfate | — | 9.52 |
| Sodium Lauroamphoacetate | — | 5.00 |
| Citric acid (anhydrous) | — | 0.93 |
| Water | Balance | Balance |

TABLE 9

Dry sheet

| Materials: | Formulation 1 | Formulation 2 |
|---|---|---|
| Polyvinyl alcohol (with a degree of polymerization of about 1700, a hydrolysis level of 88%) | 21.00 | 23.69 |
| Glycerin | 3.00 | 9.51 |
| Linear Alkylbenzene Sulfonate | 53.00 | — |
| Sodium Laureth-3 Sulfate | 10.00 | 10.42 |
| C12-C14 Ethoxylated alcohol | 10.00 | — |
| Sodium Lauryl Sulfate | — | 32.89 |
| Sodium Lauroamphoacetate | — | 17.28 |
| Citric acid (anhydrous) | — | 3.21 |
| Water | Balance | Balance |

Viscosity of the wet pre-mixture composition for Formulation 1 is about 14309.8 cps. After aeration, the average density of such aerated wet pre-mixture is about 0.25 g/cm³. Viscosity of the wet pre-mixture composition for Formulation 2 is about 19254.6 cps. After aeration, the average density of such aerated wet pre-mixture is about 0.225 g/cm³.

Flexible, porous, dissolvable solid sheet 1 and 2 are prepared from the above wet pre-mixtures as described in Table 8 using a continuous aerator (Aeros) and a rotary drum dryer with the settings and conditions as described above in Example 1 (see Table 3).

A flexible, porous, dissolvable solid sheet 3 is also prepared from the above wet pre-mixture as described in Table 8 using a continuous aerator (Oakes) and a mold placed on a hot plate (which provides bottom conduction-based heating), with the following settings and conditions as described in Table 10 below:

TABLE 10

(HOT PLATE DRYING)

| Parameters | Value |
|---|---|
| Wet pre-mixture temperature before and during aeration | 80° C. |
| Oakes air flow meter setting | 19.2 L/hour |
| Oakes pump meter speed setting | 20 rpm |
| Oakes mixing head speed | 1500 rpm |
| Mold depth | 1.0 mm |
| Hot plate surface temperature | 130° C. |
| Drying time | 12.5 min |

Further, flexible, porous, dissolvable solid sheets 4 and 5 are prepared from the above wet pre-mixtures described in Table 8 using a continuous aerator (Oakes) and a mold placed on an impingement oven with the following settings and conditions as described in Table 11 below:

TABLE 11

(IMPINGEMENT OVEN DRYING)

| Parameters | Value |
|---|---|
| Wet pre-mixture temperature before and during aeration | 80° C. |
| Oakes air flow meter setting | 19.2 L/hour |
| Oakes pump meter speed setting | 20 rpm |
| Oakes mixing head speed | 1500 rpm |
| Mold depth | 1.0 mm |
| Impingement oven temperature | 130° C. |
| Drying time | 6 min |

Tables 12-15 as follows summarize various physical parameters and pore structures measured for the Sheets 1-5 made from the above-described wet pre-mixtures and drying processes.

TABLE 12

(PHYSICAL PARAMETERS)

| Sheet | Formulation | Drying Process | Average Basis Weight g/m² | Average Density g/cm³ | Average Thickness mm | Specific Surface Area m²/g |
|---|---|---|---|---|---|---|
| 1 | Formulation 1 | Rotary Drum | 147.5 | 0.118 | 1.265 | 0.115 |
| 2 | Formulation 2 | Rotary Drum | 138.4 | 0.111 | 1.254 | 0.107 |
| 3 | Formulation 2 | Hot Plate | 216.3 | 0.111 | 1.968 | — |
| 4 | Formulation 1 | Impingement Oven | 116.83 | 0.118 | 1.002 | — |
| 5 | Formulation 2 | Impingement Oven | 212.9 | 0.111 | 1.929 | — |

TABLE 13

(OVERALL PORE STRUCTURES)

| Sheet | Formulation | Drying Process | Percent Open Cell Content % | Overall Average Pore Size μm | Average Cell Wall Thickness μm |
|---|---|---|---|---|---|
| 1 | Formulation 1 | Rotary Drum | 90.75 | 467.1 | 54.3 |
| 2 | Formulation 2 | Rotary Drum | 93.54 | 466.9 | 42.8 |
| 3 | Formulation 2 | Hot Plate | — | 287.4 | 19.7 |
| 4 | Formulation 1 | Impingement Oven | — | 197.6 | 15.2 |
| 5 | Formulation 2 | Impingement Oven | — | 325.1 | 18.7 |

TABLE 14

(SURFACE AND REGIONAL PORE STRUCTURES)

| Sheet | Formulation | Drying Process | Surface Average Pore Diameter (μm) Top | Average Pore Size (μm) | | |
|---|---|---|---|---|---|---|
| | | | | Top | Middle | Bottom |
| 1 | Formulation 1 | Rotary Drum | 201.5 | 458.3 | 479.1 | 463.9 |
| 2 | Formulation 2 | Rotary Drum | 138.2 | 412.4 | 519.0 | 469.1 |
| 3 | Formulation 2 | Hot Plate | 120.8 | 259.7 | 292.0 | 309.9 |
| 4 | Formulation 1 | Impingement Oven | 53.3 | 139.9 | 213.1 | 238.7 |
| 5 | Formulation 2 | Impingement Oven | 60.0 | 190.7 | 362.6 | 419.6 |

TABLE 15

(VARIATIONS BETWEEN REGIONAL PORE STRUCTURES)

| Sheet | Formulation | Drying Process | Cross-Region Relative STD (%) | Btw-Region Ratios of Average Pore Sizes | | |
|---|---|---|---|---|---|---|
| | | | | Bottom-to-Top | Bottom-to-Middle | Middle-to-Top |
| 1 | Formulation 1 | Rotary Drum | 2.31% | 1.012 | 0.968 | 1.046 |
| 2 | Formulation 2 | Rotary Drum | 11.43% | 1.137 | 0.904 | 1.259 |
| 3 | Formulation 2 | Hot Plate | 8.84% | 1.193 | 1.061 | 1.124 |
| 4 | Formulation 1 | Impingement Oven | 25.99% | 1.706 | 1.120 | 1.523 |
| 5 | Formulation 2 | Impingement Oven | 36.74% | 2.200 | 1.157 | 1.901 |

The above data demonstrates that when the heating direction is offset from the gravitation direction during most of the drying step, the resulting solid sheets (e.g., Sheets 1, 2 and 3) may have a top surface with larger pore openings and reduced pore size variations in different regions along the direction across the thickness of such sheet article compared to the solid sheet articles obtained when the heating direction is substantially aligned with the gravitational direction (e.g., Sheets 4 and 5). Particularly, the above tables show that Sheets 1, 2 and 3 have Top Surface Average Pore Diameters of greater than 100 nm, while the Sheets 4 and 5 do not.

Example 4: Exemplary Solid Sheet Articles

The following are examples of solid sheet articles. The Sheets I to V with the formulations as shown in Table 16 below are prepared similarly as Example 1. Further, multi-layer sheet articles with 2-20 layers each may be formed by stacking the respective sheets.

TABLE 16

| Materials (wt %) | Sheet I | Sheet II | Sheet III | Sheet IV | Sheet V |
|---|---|---|---|---|---|
| PVA | 22.3 | 25.8 | 19.7 | 22.3 | 24.7 |
| Glycerin | 34.4 | 35.1 | 33.2 | 34.4 | 34.6 |
| DEEDMAC | 31.1 | 23.5 | 30.0 | — | 25.4 |
| HTQ | — | — | — | 31.1 | — |

TABLE 16-continued

| Materials (wt %) | Sheet I | Sheet II | Sheet III | Sheet IV | Sheet V |
|---|---|---|---|---|---|
| Starch | 2.2 | 3.5 | 4.6 | 2.2 | 3.3 |
| Neat Perfume | — | 2.1 | — | — | — |
| Perfume Microcapsule | — | — | 2.5 | — | 2.0 |
| Water Content | Balance | Balance | Balance | Balance | Balance |

Additionally, solid sheet articles containing coating compositions (i.e., juice) may be prepared by applying one or more of the Juice i to v as shown in Table 17 below between the sheets (e.g. one or more of Sheets I to V) during stacking the sheets. An exemplary solid sheet article containing a coating composition may be prepared by applying the Juice i between Sheets I.

TABLE 17

| Materials (wt %) | Juice i | Juice ii | Juice iii | Juice iv | Juice v |
|---|---|---|---|---|---|
| Silicone | 35.5 | — | 40 | — | 35.5 |
| Neat Perfume | 52 | 52 | 30 | 20 | 30 |
| Perfume Microcapsule | — | — | — | 30 | 20 |
| AE7 | — | 35.5 | 30 | 35.5 | — |
| Silicon dioxide | 12.5 | 12.5 | — | 12.5 | 12.5 |
| Water Content | Balance | Balance | Balance | Balance | Balance |

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A process of making a solid sheet article, wherein the process comprises:
   a) preparing a wet pre-mixture comprising a water-soluble polymer comprising polyvinyl alcohol, a plasticizer comprising glycerin, a cationic surfactant comprising diethyl ester dimethyl ammonium chloride, starch, and water, wherein the weight ratio of said plasticizer over said cationic surfactant is from 1.0 to 1.8;
   b) aerating said wet pre-mixture to form an aerated wet pre-mixture;
   c) forming said aerated wet pre-mixture into a sheet having opposing first and second sides; and
   d) drying said formed sheet to make the solid sheet article.

2. The process of making a solid sheet article of claim 1, wherein the weight ratio of said plasticizer over said cationic surfactant is from 1.2 to about 1.6.

3. The process of claim 1, wherein said water-soluble polymer further comprises a polyvinylpyrrolidone, a polyalkylene oxide, a pullulan, a gelatin, a hydroxypropylmethylcellulose, a methycellulose, a carboxymethycellulose, or a combination thereof.

4. The process of claim 1, wherein the water-soluble polymer comprises from about 5% to about 50% of a polyvinyl alcohol by total weight of said solid sheet article.

5. The process of claim 1, wherein said solid sheet article comprises from about 10% to about 40%, of said polyvinyl alcohol, and from about to about 4.5%, of said starch, by total weight of said solid sheet article.

6. The process of claim 1, wherein the water-soluble polymer comprises from about 2% to about 30% by total weight of said solid sheet article of a first polyvinyl alcohol having a first weight average molecular weight of about 15,000 to about 35,000 Daltons and from about 6% to about 30% by total weight of said solid sheet article of a second polyvinyl alcohol having a second weight average molecular weight of about from 50,000 to about 150,000 Daltons.

7. The process of claim 1, wherein said solid sheet article further comprises from about 0.5% to about 8% of a non-ionic surfactant by total weight of said solid sheet article.

8. The process of claim 1, wherein said solid sheet article is characterized by:
   a Percent Open Cell Content of from about 85% to about 100%;
   an Overall Average Pore Size of from about 150 μm to about 1000 μm;
   an Average Cell Wall Thickness of from about 5 μm to about 200 μm;
   a final moisture content of from about 0.5% to about 25% by weight of said solid sheet article;
   a thickness of each sheet being from about 0.5 mm to about 4 mm;
   a basis weight of from about 50 grams/m 2 to about 250 grams/m$^2$;
   a density of from about 0.05 grams/cm 3 to about 0.5 grams/cm$^3$;
   a Specific Surface Area of from about 0.03 m$^2$/g to about 0.25 m$^2$/g; or
   a combination thereof.

9. The process of claim 1, wherein said cationic surfactant further comprises behenyl trimethyl ammonium chloride; stearyl trimethyl ammonium chloride; cetyl trimethyl ammonium chloride; lauryl trimethyl ammonium chloride; hydrogenated tallow alkyl trimethyl ammonium chloride, dimethyl hydroxyethyl lauryl ammonium chloride; dialkyl (14-18) dimethyl ammonium chloride; ditallow alkyl dimethyl ammonium chloride; dihydrogenated tallow alkyl dimethyl ammonium chloride; distearyl dimethyl ammonium chloride; dicetyl dimethyl ammonium chloride; N,N-di(acyl-oxy ethyl)-N,N-dimethylammonium chloride; N,N-di(acyl-oxyisopropyl)-N,N-dimethylammonium methyl sulfate; N,N-di(acyl-oxyethyl)-N,N-methylhydroxyethylammonium methylsulfate; or a combination thereof.

10. The process of making a solid sheet article of claim 1, wherein the step d) is conducted for a duration from about 5 min to about 300 min, at a temperature from about 70° C. to about 200° C., along a heating direction that forms a temperature gradient decreasing from the first side to the second side of the formed sheet, wherein the heating direction is substantially opposite to the gravitational direction for more than half of the drying time.

11. The process of making a solid sheet article of claim 1, wherein the wet pre-mixture has a viscosity of from about 1,000 cps to about 25,000 cps measured at 40° C. and 1 s$^{-1}$.

12. The process of making a solid sheet article of claim 1, wherein the aerated wet pre-mixture has a density of about 0.05 g/ml to about 0.7 g/ml.

13. The process of making a solid sheet article of claim 1, wherein the aerated wet pre-mixture has a density of about 0.2 g/ml to about 0.5 g/ml.

14. The process of making a solid sheet article of claim 1, wherein the aerated wet pre-mixture has a density of about 0.25 g/ml to about 0.45 g/ml.

* * * * *